US011826578B2

(12) United States Patent
Kim et al.

(10) Patent No.: US 11,826,578 B2
(45) Date of Patent: Nov. 28, 2023

(54) NITROGEN-BASED, LOW-TEMPERATURE ATMOSPHERIC PRESSURE PLASMA FOR TREATING MUSCLE DAMAGE

(71) Applicant: AJOU UNIVERSITY INDUSTRY-ACADEMIC COOPERATION FOUNDATION, Gyeonggi-do (KR)

(72) Inventors: Chul Ho Kim, Seoul (KR); Sung Un Kang, Gyeonggi-do (KR); Jae Won Choi, Gyeonggi-do (KR)

(73) Assignee: Ajou University Industry-Academic Cooperation Foundation

( * ) Notice: Subject to any disclaimer, the term of this patent is extended or adjusted under 35 U.S.C. 154(b) by 0 days.

(21) Appl. No.: 17/559,017

(22) Filed: Dec. 22, 2021

(65) Prior Publication Data

US 2022/0111221 A1 Apr. 14, 2022

Related U.S. Application Data

(62) Division of application No. 15/750,932, filed as application No. PCT/KR2016/008811 on Aug. 10, 2016, now abandoned.

(30) Foreign Application Priority Data

Aug. 10, 2015 (KR) ......................... 10-2015-0112564

(51) Int. Cl.
 *A61N 1/44* (2006.01)
 *A61K 33/00* (2006.01)
 *C12N 5/077* (2010.01)

(52) U.S. Cl.
 CPC ............... *A61N 1/44* (2013.01); *A61K 33/00* (2013.01); *C12N 5/0658* (2013.01); *C12N 2500/02* (2013.01)

(58) Field of Classification Search
 CPC ...... A61N 1/44; A61N 1/0472; A61N 1/0468; A61K 33/00; A61K 31/443; A61K 31/4525; A61K 31/47; A61K 31/4709; A61K 45/06; A61K 2300/00; C12N 5/0658; C12N 2500/02; B01J 19/08; B01J 19/088; C01B 21/20; C01B 21/24; C01B 21/203; C01B 21/265; H05H 1/2406; H05H 1/245; H05H 1/2465; A61P 29/00; A61P 31/00; A61P 7/02; A61P 35/00; A61L 29/06; A61L 31/06; A61L 29/146; A61L 31/146; A61L 2300/608; A61L 27/54; A61L 31/16; A61L 29/16; A61L 2300/114

See application file for complete search history.

(56) References Cited

U.S. PATENT DOCUMENTS

| 6,967,102 B1* | 11/2005 | Anderson ......... G01N 33/5008 514/753 |
| 8,460,283 B1 | 6/2013 | Laroussi et al. |
| 2010/0023111 A1 | 1/2010 | Kondyurin et al. |
| 2011/0159116 A1* | 6/2011 | Reynolds ............... A61K 33/00 423/405 |
| 2012/0296265 A1 | 11/2012 | Dobrynin et al. |
| 2015/0366042 A1 | 12/2015 | Zaidi |
| 2018/0229047 A1 | 8/2018 | Kim et al. |

FOREIGN PATENT DOCUMENTS

| KR | 10-2008-0004452 | 1/2008 |
| KR | 10-2015-0084146 | 7/2015 |
| WO | WO 2015/066278 | 5/2015 |

OTHER PUBLICATIONS

Choi et al. "Novel Therapeutic Effects of Non-thermal atmospheric pressure plasma for Muscle Regeneration and Differentiation," Scientific Reports, Jun. 2016, vol. 6, 28829, 11 pages.
Park et al. "Plasma Medicine: How can Nonthermal Atmospheric Plasma be Applied to Medicine," Journal of Life Science, 2013, vol. 23, No. 6, pp. 838-846 (English abstract and figures).
International Search Report prepared by the Korean Intellectual Property Office dated Dec. 8, 2016, for International Application No. PCT/KR2016/008811.
Official Action for U.S. Appl. No. 15/750,932, dated May 1, 2020 7 pages Restriction Requirement.
Official Action for U.S. Appl. No. 15/750,932, dated Jul. 17, 2020 8 pages.
Official Action for U.S. Appl. No. 15/750,932, dated Dec. 18, 2020 9 pages.
Official Action for U.S. Appl. No. 15/750,932, dated May 17, 2021 8 pages.
Official Action for U.S. Appl. No. 15/750,932, dated Aug. 26, 2021 7 pages.

* cited by examiner

*Primary Examiner* — Xiuyu Tai
(74) *Attorney, Agent, or Firm* — Sheridan Ross P.C.

(57) ABSTRACT

The present invention relates to a method for producing a nitrogen-based non-thermal atmospheric pressure plasma for treating damaged muscles or promoting regeneration of damaged muscles, and to a method for treating damaged muscle or promoting regeneration of damaged muscles using the atmospheric pressure plasma. The nitrogen-based non-thermal atmospheric pressure plasma according to the present invention can effectively induce muscle cell activation, migration of muscle cells to damaged sites, muscle cell proliferation, and muscle cell differentiation, without surgical operation or during a treatment procedure after surgical operation, and thus can be advantageously used as a novel therapeutic agent and therapeutic method against muscle damage and muscle damage-associated diseases.

6 Claims, 14 Drawing Sheets

FIG. 13

|  | 7d | | 14d | |
|---|---|---|---|---|
|  | L | R | L | R |
| C | | | | |
| G | | | | |
| P30 | | | | |
| P60 | | | | |

Pax 7: red
Myo D: green

Myo G: red
Myo D: green

NITROGEN-BASED, LOW-TEMPERATURE ATMOSPHERIC PRESSURE PLASMA FOR TREATING MUSCLE DAMAGE

CROSS REFERENCE TO RELATED APPLICATIONS

This application is a divisional of U.S. patent application Ser. No. 15/750,932, filed Feb. 7, 2018, now abandoned, which is a national stage application under 35 U.S.C. 371 and claims the benefit of PCT Application No. PCT/KR2016/008811 having an international filing date of 10 Aug. 2016, which designated the United States, which PCT application claimed the benefit of South Korea Patent Application No. 10-2015-0112564 filed 10 Aug. 2015, the disclosures of each of which are incorporated herein by reference.

TECHNICAL FIELD

The present invention relates to a method for producing a nitrogen-based non-thermal atmospheric pressure plasma for treating damaged muscles or promoting regeneration of damaged muscles, and to a method for treating damaged muscle or promoting regeneration of damaged to muscles using the atmospheric pressure plasma.

The present invention is derived from research conducted as part of the Ministry of Science and ICT's mid-career researcher support project [Project Identification Number: 1711181511, Project Number: 2023R1A2C3002835, Research Project Name: Discovery of mechanisms for controlling cancer and cancer microenvironment metabolic heterogeneity based on transcriptome profiling in intractable head and neck cancer and development of patient-customized antibody treatment], the Ministry of Health and Welfare's research-oriented hospital development (R&D) project [Project Identification Number: 1465034377, Project Number: HR21C1003 (HR21C1003010021), Research Project Name: Establishment of a Quattro win-win platform based on the 5th industrial revolution hyper-personalized HI future technology (Establishment of customized healing innovation HI (Human Interface) early technology commercialization platform)], and the Korea Environmental Industry and Technology Institute Environmental Technology Department's environmental technology development project for treating medical waste with infection concerns [as of 2023, Project Identification Number: 1485019434 / as of 2022, Project Identification Number: 1485018669, Project Number: 2021003350001, Research Project Name: Demonstration of an autonomous robot system for processing medical waste with infection concerns and development of plasma disinfection water harmless to the human body].

BACKGROUND ART

Generally, muscle injuries include various injuries such as contusions (bruises), lacerations, ischemia, and complete ruptures. These injuries may cause tremendous pain and can incapacitate the affected persons, preventing them from being able to go to work or even to participate in normal daily activities. Particularly, of the acute injuries to skeletal muscles, strains (also known as stretch-induced injuries) are most common. Strains can account for 30% or more of all injures treated by occupational or sports medicine professionals. A muscle strain injury is characterized by disruption of a muscle-tendon unit. The disruption of the muscle-tendon unit may occur anywhere on the muscle.

Muscle tissue includes cells having the properties of stem cells called "satellite cells" which reside between the sarcolemma and the basal lamina. In a normal muscular state these cells exist in an inactive resting state, and when muscle damage occurs, these cells proliferate and differentiate to help regenerate damaged muscle. However, when extensive and deep damage occurs, there is a limit to the spontaneous muscle regeneration by cellular migration and proliferation. Thus, studies have been conducted on various therapeutic agents and therapeutic methods to treat muscle damage by promoting muscle regeneration and to induce muscle regeneration. However, methods such as stem cell transplantation, which have been studied for muscle tissue regeneration and the like, have a limitation in that they cannot be easily applied to patients because they involve surgical procedures. Therefore, there is a need for therapeutic agents and treatment methods for regenerating muscle and treating muscle damage by non-invasive methods.

"Non-thermal atmospheric pressure plasma" refers to a state in which electrons among plasma ions and electrons have energy greater than the energy of the ions. Specifically, "non-thermal plasma" is generated by the change in valence electron state of molecules of a gas, which is caused by bombardment of the molecules with electrons generated from the gas by high-voltage electric discharge. Thus, the non-thermal plasma is an electrically neutral gas composed of positively or negatively charged radicals (e.g., OH, COOH, CHO, etc.), excited molecules, or ions, which are highly reactive chemical species.

Plasmas are classified into two categories: high-temperature thermal plasma in which electrons, ions and molecules all have high temperature; and non-thermal plasma in which only electrons have high temperature. The high-temperature thermal plasma makes it possible to obtain high temperature, and thus is used mainly to melt materials, and the non-thermal plasma has advantages in that, because only the temperature of electrons therein is high, it may be applied to materials or conditions to which high temperature may not be applied, and in that it provides a simple device.

Such plasmas induce various chemical reactions, and thus studies have been actively conducted to apply such plasmas to various fields. However, a method of treating damaged muscle tissue or the like by use of such plasmas is not yet known.

DISCLOSURE

Technical Problem

Therefore, it is an object of the present invention to provide a method for producing a nitrogen-based non-thermal atmospheric pressure plasma for a novel therapeutic agent and therapeutic method which is capable of treating muscle damage or muscle damage-associated diseases without surgical operation.

Another object of the present invention is to provide a nitrogen-based non-thermal atmospheric pressure plasma for treating damaged muscles or promoting regeneration of damaged muscles, produced by the method.

Still another object of the present invention is to provide a pharmaceutical composition for treating muscle damage-associated diseases, and a method for treating damaged muscles or promoting regeneration of damaged muscles, winch comprise the nitrogen-based non-thermal atmospheric pressure plasma.

Yet another object of the present invention is to provide a method of promoting migration, proliferation or differentiation of muscle cells, which uses the nitrogen-based non-thermal atmospheric pressure plasma.

Technical Solution

The present invention provides a method for producing a nitrogen-based non-thermal atmospheric pressure plasma for treating damaged muscles or promoting regeneration of damaged muscles, the method comprising the steps of: introducing nitrogen gas as a carrier gas; and applying a discharge initiation voltage of 5 to 10 kV to the introduced nitrogen gas at a frequency of 5 to 20 kHz, thereby producing a nitrogen-based non-thermal atmospheric pressure plasma.

The present invention also provides a nitrogen-based non-thermal atmospheric pressure plasma for treating damaged muscles or promoting regeneration of damaged muscles, produced by the method.

The present invention also provides a method for treating damaged muscles or promoting regeneration of damaged muscles, which comprise the nitrogen-based non-thermal atmospheric pressure plasma.

The present invention also provides a pharmaceutical composition for treating muscle damage-associated diseases, which comprise the nitrogen-based non-thermal atmospheric pressure plasma.

The present invention also provides a method of promoting migration, proliferation or differentiation of muscle cells, the method comprising a step of treating muscle cells in vitro with the nitrogen-based non-thermal atmospheric pressure plasma for treating damaged muscles or promoting regeneration of damaged muscles Advantageous Effects The nitrogen-based non-thermal atmospheric pressure plasma according to the present invention can effectively induce muscle cell activation, migration of muscle cells to damaged sites, muscle cell proliferation and muscle cell differentiation, without surgical operation or during a treatment procedure after surgical operation, and thus can be advantageously used as a novel therapeutic agent and therapeutic method against muscle damage and muscle damage-associated diseases.

DESCRIPTION OF DRAWINGS

FIG. 13 shows the results of PSR staining performed to confirm that tissue appearing to be new muscle develops after nitrogen-based non-thermal atmospheric pressure plasma treatment (C: untreated control group; G: group treated with nitrogen gas alone; P30, group treated for 30 seconds. P60: group treated for 60 seconds). Scale bar=1000 μm.

BEST MODE

The present invention provides a method for producing a nitrogen-based non-thermal atmospheric pressure plasma for treating damaged muscles or promoting regeneration of damaged muscles, the method comprising the steps of: introducing nitrogen gas as a carrier gas: and applying a discharge initiation voltage of 5 to 10 kV to the introduced nitrogen gas at a frequency of 5 to 20 kHz, thereby producing a nitrogen-based non-thermal atmospheric pressure plasma.

The present invention also provides a nitrogen-based non-thermal atmospheric pressure plasma for treating damaged muscles or promoting regeneration of damaged muscles, produced by the method.

When damaged muscle sites are treated with the nitrogen-based non-thermal atmospheric pressure plasma of the present invention, the nitrogen-based non-thermal atmospheric pressure plasma can effectively induce muscle cell activation, migration of muscle cells to the damaged sites, muscle cell proliferation, and muscle cell differentiation. Thus, the nitrogen-based non-thermal atmospheric pressure plasma can be advantageously used for treatment of muscle damage and muscle damage-associated diseases.

The term "plasma" refers to an ionized gas that satisfies the Debye shielding. Plasma is considered as one of the four fundamental states of matter (the others being gas, liquid, and solid), and is designated as the fourth state. The plasma of the present invention is generated from a neutral gas by phase transition induced by application of an external voltage, and may comprise electrons and cations generated by excitation and ionization of the neutral gas, and may also comprise radicals produced by excitation of the molecular gas.

As a system for producing the plasma any known plasma producing system may be used without limitations as long as it can produce the nitrogen-based non-thermal atmospheric pressure plasma according to the purpose of the present invention.

The plasma producing system of the present invention may comprise an optical emission spectroscope, an oscilloscope, a high-voltage probe, an AC clamp current meter, a plasma jet device, an UV and gas sensor, and a carrier gas supply unit. Each electrode that is used in the present invention may be a disc-shaped electrode having a diameter 5 to 10 mm and a thickness of 150 to 250 μm and having 19 through-holes with a size of 300 to 600 μm. Between the electrodes, a ceramic spacer serving as an insulating layer may be provided which has an outer diameter of 5 to 20 mm, an inner diameter of 5 to 10 mm, and a thickness of 0.5 to 2 mm.

Figure 2:
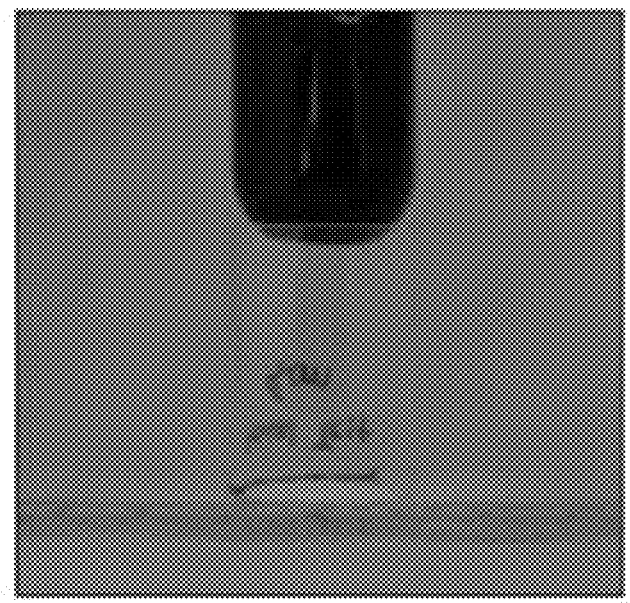
FIG. 2 shows the configuration of a plasma device comprising a shielding tube connected to a plasma nozzle, and also shows a state in which plasma treatment is performed using the plasma device.

In particular, in the present invention, a device for applying the plasma to a muscle defect site was designed such that it makes it possible to check the state of the plasma applied to the defect site and prevents the plasma from leaking from the defect site. Specifically, a plasma device comprising a shielding tube connected to a plasma nozzle was used for plasma irradiation. The configuration of this plasma device is shown in FIG. 2.

The "carrier gas" is a gas that is used to produce the plasma according to the purpose of the present invention. The plasma can be produced by supplying high-voltage current to this gas. The carrier gas that is used in the present invention is a nitrogen gas.

In the present invention, conditions for exposure to the nitrogen-based non-thermal atmospheric pressure plasma for treating muscle damage may be adjusted depending on the amount of plasma gas discharged, the kind of carrier gas, the distance from a plasma source to a defect site, the number of exposures to the plasma, and plasma exposure time.

The plasma producing system according to the present invention may use a discharge initiation voltage of 5 to 10 kV, preferably 7 to 8 kV. After discharge initiation, the plasma producing system may use a voltage of 1 to 10 kV, preferably 2 to 5 kV, more preferably 3 to 4 kV, at which the plasma is stably discharged. A suitable frequency that is used to produce the plasma according to the present invention is 5 to 20 kHz, preferably 10 to 20 kHz, most preferably 15 kHz.

This plasma producing system generates a non-thermal plasma (NTS) at atmospheric pressure.

As used herein, "damaged muscles" may include damage to any muscle tissue. Muscle damage may result from physical trauma to muscle tissue, due to an accident, a sports injury, endocrine disorders, disease, wound, or surgery.

The nitrogen-based non-thermal atmospheric pressure plasma according to the present invention has the effect of treating damaged muscles by one or more selected from the group consisting of muscle cell activation, migration of muscle cells to a damaged site, muscle cell proliferation, and muscle cell differentiation.

Therefore, the nitrogen-based non-thermal atmospheric pressure plasma according to the present invention is useful for repairing muscles and treating muscle damage by promoting regeneration of damaged muscles. The method of the present invention is also useful for muscle spasm relief. In particular, the nitrogen-based non-thermal atmospheric pressure plasma according to the present invention directly triggers muscle cell activation and promotes muscle tissue regeneration, unlike general muscle contraction strengthening, and has a very excellent effect of repairing or regenerating muscle tissue in defect sites. Thus, the nitrogen-based non-thermal atmospheric pressure plasma according to the present invention can be effectively used for treatment of patients having muscle damage and muscle damage-associated diseases, which are caused by muscle tissue death, muscle cell death or the like. The treatment according to the present invention includes preventive, palliative and curative treatments.

The present invention also provides a method for treating damaged muscles or promoting regeneration of damaged muscles in a subject, the method comprising a step of treating a damaged muscle site with the nitrogen-based non-thermal atmospheric pressure plasma for treating damaged muscles or promoting regeneration of damaged muscles, produced by the above-described method.

The subject is a subject having muscle damage caused by various factors such as an accident, a sports injury, endocrine disorders, disease, wound, or surgery. When the subject is treated with the nitrogen-based non-thermal atmospheric pressure plasma of the present invention, muscle cell activation, migration of muscle cells to a damaged site, muscle cell proliferation and muscle cell differentiation may actively occur, thereby inducing muscle tissue regeneration and differentiation.

For treatment of muscle damage in the subject, conditions for exposure to the nitrogen-based non-thermal atmospheric pressure plasma of the present invention may be controlled.

Although the amount of nitrogen-based non-thermal atmospheric pressure plasma gas discharged may be suitably selected so as to be effective for treatment of muscle damage, it is preferably 2 to 10 L/min, more preferably 3 to 6 L/min.

Furthermore, in the present invention, the distance from a plasma source to a defect site to be treated against muscle damage may be 0.3 to 10 cm, preferably 0.3 to 5 cm. Even when the nitrogen-based non-thermal atmospheric pressure plasma of the present invention is irradiated to a defect site, it induces no fever phenomenon, and thus has an advantage in that the plasma can be irradiated from a position adjacent to a damaged muscle site.

In addition, conditions for treatment with the nitrogen-based non-thermal atmospheric pressure plasma of the present invention may include treating a damaged muscle site with the plasma 1 to 10 times a day, preferably 1 to 5 times a day, for 5 to 300 seconds, preferably 10 to 200 seconds, more preferably 10 to 120 seconds.

The nitrogen-based non-thermal atmospheric pressure plasma for treating damaged muscles or promoting regeneration of damaged muscles according to the present invention is characterized in that it is produced using a nitrogen ($N_2$) gas as a carrier gas. The plasma produced using nitrogen gas has advantages over plasmas, produced using other carrier gases, in that it can achieve better effects, including regeneration of damaged muscles, promotion of new muscle formation, promotion of muscle cell migration, and muscle cell differentiation, without causing cytotoxicity.

In a preferred embodiment of the present invention, the nitrogen-based non-thermal atmospheric pressure plasma is produced using a nitrogen gas as a carrier gas, and may be produced and discharged under the following conditions: an initiation voltage of 7 to 8 kV, a stable voltage of 3 to 4 kV, a frequency of 15 kHz, and a plasma discharge amount of 3 to 6 L/min. The distance from a plasma source, from which the plasma is discharged, to a defect site to be treated against muscle damage, may be controlled to 0.3 to 5 cm. In addition, treatment with the plasma may be performed once for 10 to 120 seconds a day, and the period of treatment with the plasma may be suitably adjusted depending on the degree of repair of damaged muscles.

The present invention also provides a pharmaceutical composition for treating muscle damage-associated diseases, comprising the nitrogen-based non-thermal atmospheric pressure plasma.

The muscle damage-associated diseases refer to a collection of diseases caused by damaged muscles, and may include muscle cell death caused by various factors, diseases caused by damage to muscle tissue, and the like. The muscle damage-associated diseases may include, without limitation, all muscle damage-associated diseases for which treatment with the nitrogen-based non-thermal atmospheric pressure plasma can promote muscle tissue differentiation and activate muscle cells, thereby treating muscle damage. Typical examples of the muscle damage-associated diseases include ligament rupture, ligament damage, rotator cuff damage, and the like.

The nitrogen-based non-thermal atmospheric pressure plasma according to the present invention may be used in combination with primary therapy, for example, chemical therapy or surgery, thereby inducing the more rapid action of the primary therapy and enhancing the muscle damage repair action of the primary therapy. Thus, the nitrogen-based non-thermal atmospheric pressure plasma according to the present invention may be either used to enhance the effect of a main therapeutic agent that is primarily used in drug-based chemotherapy, or applied directly to a site in need of muscle repair without surgery.

The present invention also provides a kit for treating muscle damage, comprising the system for producing the nitrogen-based non-thermal atmospheric pressure plasma.

The kit may be used to treat muscle damage by muscle repair, and is preferably a kit for non-invasively treating a damaged muscle site directly with the nitrogen-based non-thermal atmospheric pressure plasma. Since the kit of the present invention comprises a system capable of generating the nitrogen-based non-thermal atmospheric pressure plasma, if required, it makes it possible to apply the plasma to a site in need of treatment, thereby facilitating the treatment of muscle damage and muscle damage-associated diseases.

As used herein, the term "treatment" refers to irradiating the generated nitrogen-based non-thermal atmospheric pressure plasma directly to a lesion site, a damaged muscle site, or a site in need of muscle repair.

The kit may comprise a system for producing the nitrogen-based non-thermal atmospheric pressure plasma, and may also comprise instructions describing a method for using the system.

The present invention also provides a method for promoting migration, proliferation or differentiation of muscle cells, the method comprising a step of treating the muscle cells with the nitrogen-based non-thermal atmospheric pressure plasma for treating damaged muscles or promoting regeneration of damaged muscles.

Treatment with the nitrogen-based non-thermal atmospheric pressure plasma may be performed both in vitro and in vivo, and can effectively promote migration, proliferation or differentiation of muscle cells in subject or isolated cells, thereby ultimately inducing muscle regeneration.

In the case of muscle cells present in vitro after ex vivo isolation, these cells may be cultured in growth medium or differentiation medium, preferably growth medium. As the growth medium, any medium known in the art, which satisfies conditions for growth of muscle cells, may be used without limitations.

Hereinafter, preferred Examples and Experimental Examples will be described in order to facilitate understanding of the present invention. However, these Examples and Experimental Examples are provided merely for better understanding of the present invention, and the scope of the present invention is not limited by these Examples and Experimental Examples.

Experimental Example 1: Production of Non-Thermal Atmospheric Pressure Plasma

Figure 1:
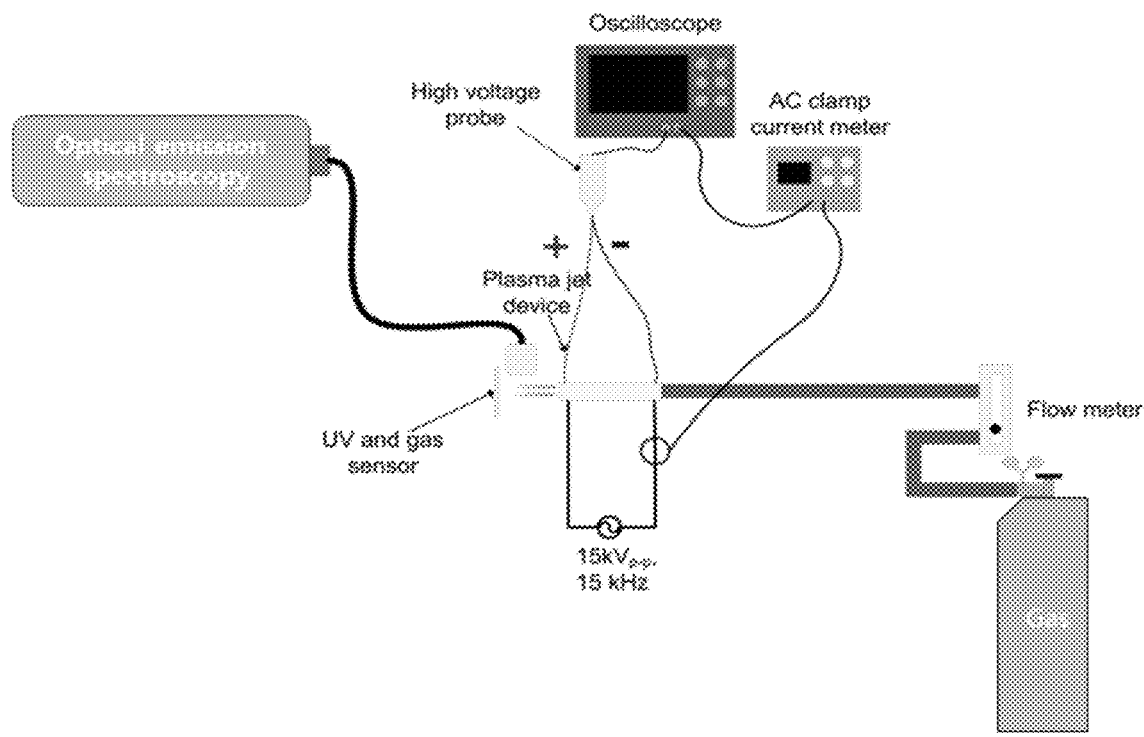
FIG. 1 illustrates a system for producing a nitrogen-based non-thermal atmospheric pressure plasma.

To produce a non-thermal atmospheric pressure plasma as a homogeneous plasma for application to biological studies, nitrogen ($N_2$) gas was used as a carrier gas. FIG. 1 shows a system for producing a nitrogen gas-based non-thermal atmospheric pressure plasma (NTP) using nitrogen gas as a carrier gas. As shown in FIG. 1, the system for producing a nitrogen-based non-thermal atmospheric pressure plasma according to the present invention comprises an optical emission spectroscope, an oscilloscope, a high-voltage probe, an AC clamp current meter, a plasma jet device, an UV and gas sensor, and a carrier gas supply unit. More specifically, each electrode that is used to produce a nitrogen-based plasma according to the present invention consists of a disc-shaped electrode having a diameter of 8 mm and a thickness of 200 μm and having 19 through-holes with a size of 500 μm, and a ceramic spacer that is used in the present invention consists of a donut-shaped structure having an outer diameter of 11 mm, an inner diameter of 6 mm and a thickness of 1 mm, and serves as an insulating layer between two electrodes. It was fond that a discharge initiation voltage for initiating plasma discharge is 7 to 8 kV and that a voltage at which the plasma is stably discharged after discharge initiation is 3 to 4 kV. A suitable frequency that is used to produce the plasma is 15 kHz. A device for applying the plasma to a defect site was designed such that it makes it possible to check the state of the plasma applied to the defect site and prevents the plasma from leaking from the defect site. Specifically, a plasma device comprising a shielding tube connected to a plasma nozzle was used for plasma irradiation. The configuration of this plasma device is shown in FIG. 2.

For the generated nitrogen-based non-thermal atmospheric pressure plasma, spectral analysis was performed using an optical emission spectroscope (SC2100, K-MAC, Korea). In addition, temperature changes occurring at different distances were analyzed with a non-contact IR thermometer (Raytek, Santa Cruz, USA). Gas was discharged at a rate of 4 L/min.

Figure 3:
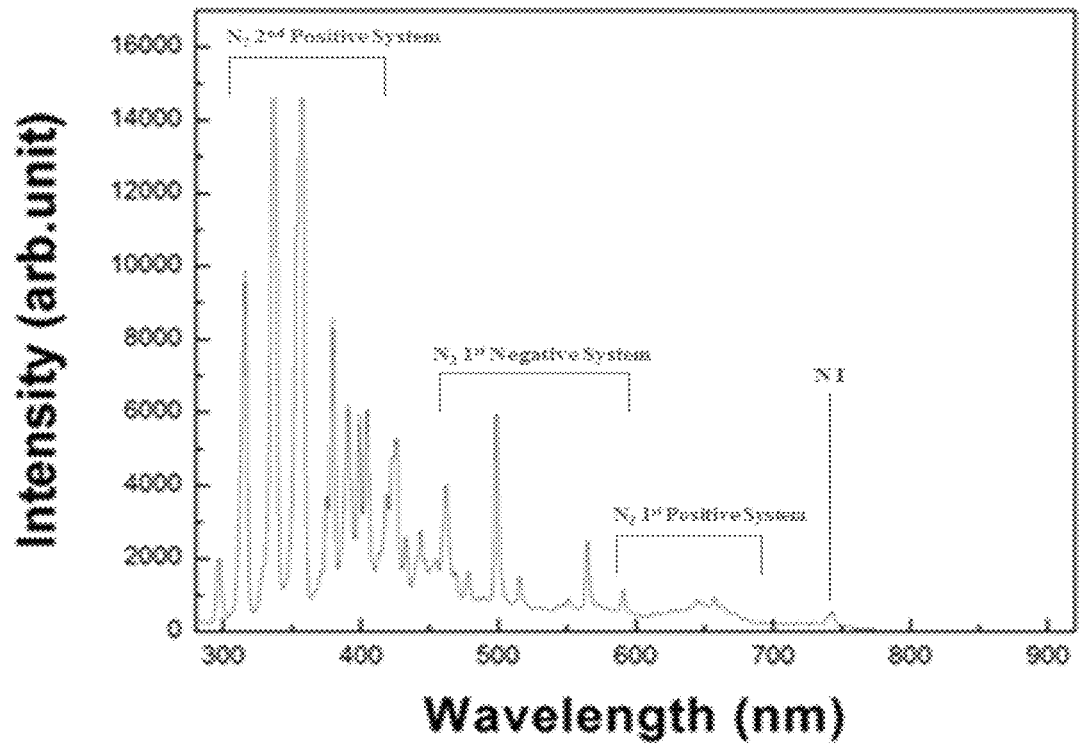
FIG. 3 shows the results of spectral analysis of nitrogen-based plasma.
Figure 4:
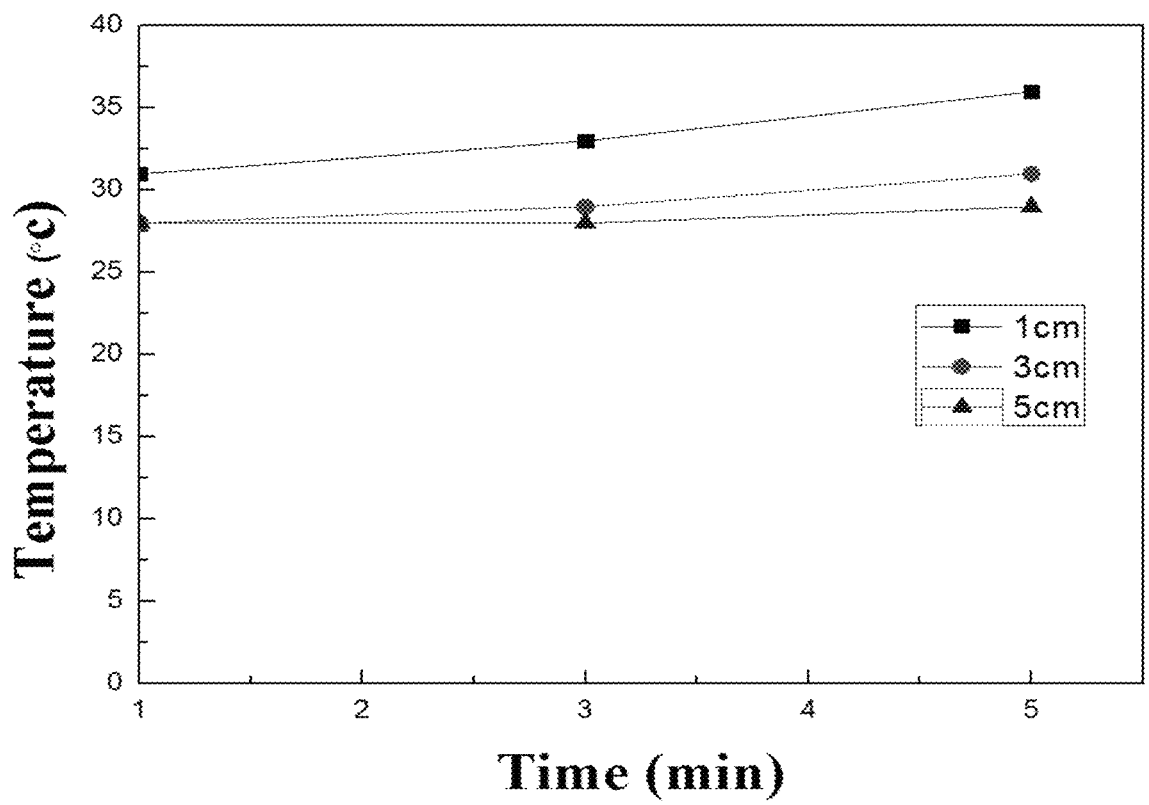
FIG. 4 shows temperature changes at irradiation distances in treatment with a nitrogen-based plasma.

FIG. 3 shows the results of spectral analysis of the nitrogen-based plasma, and FIG. 4 shows temperature changes at an irradiation distance of 1 to 5 cm. As shown in FIG. 3, a variety of excited species were observed in the plasma jet, and as shown in FIG. 4, it was found that the maximum temperature was 37° C., similar to human body temperature, even at an irradiation distance of 1 cm.

The nitrogen-based non-thermal atmospheric plasma (hereinafter referred to as nitrogen-based plasma) was used in the following experiments. A defect site or a site to be tested was treated with a nitrogen-based non-thermal atmospheric pressure plasma produced by controlling the discharge rate of high-pressure nitrogen, introduced into the inlet of a controller, to 3 to 6 L/min by use of a pressure gauge.

Experimental Example 2: Preparation of Muscle Damage Animal Model

In order to investigate whether the produced nitrogen-based plasma can treat muscle damage, muscle damage animal models were prepared, and experiments were performed. All experiments were approved by the Committee for Ethics in Animal Experiments of the Ajou University School of Medicine. Animals were cared individually in a pathogen-free environment. Each group was analyzed randomly at 7 days and 14 days post-injury. The animals in all groups remained healthy during the experimental period without disorder.

Twenty 8-week-old Sprague Dawley (SD) rats (KOATECH) were anesthetized with tiletamine (8.0 mg/kg; Virbac, Carros, France), zolazepam (8.0 mg/kg: Virbac, Carros, France) and xylazine hydrochloride (1.5 mg/kg: Bayer, Ansan, Korea). Defect sites were maintained at a distance of 20 mm from each other in order to avoid biological interference with other defect sites. To induce the panniculus camosus muscle defect on the same point of all rats, four square coordinates (each 2 cm×2 cm) were assigned based on the bones of the pelvic girdle. Muscle defects were induced on the four coordinates by removing muscles from the four sites by use of a biopsy punch having an 8 mm diameter. The induced muscle defect sites were divided into four groups at the same position, and are shown in FIG. 5.

Figure 5:
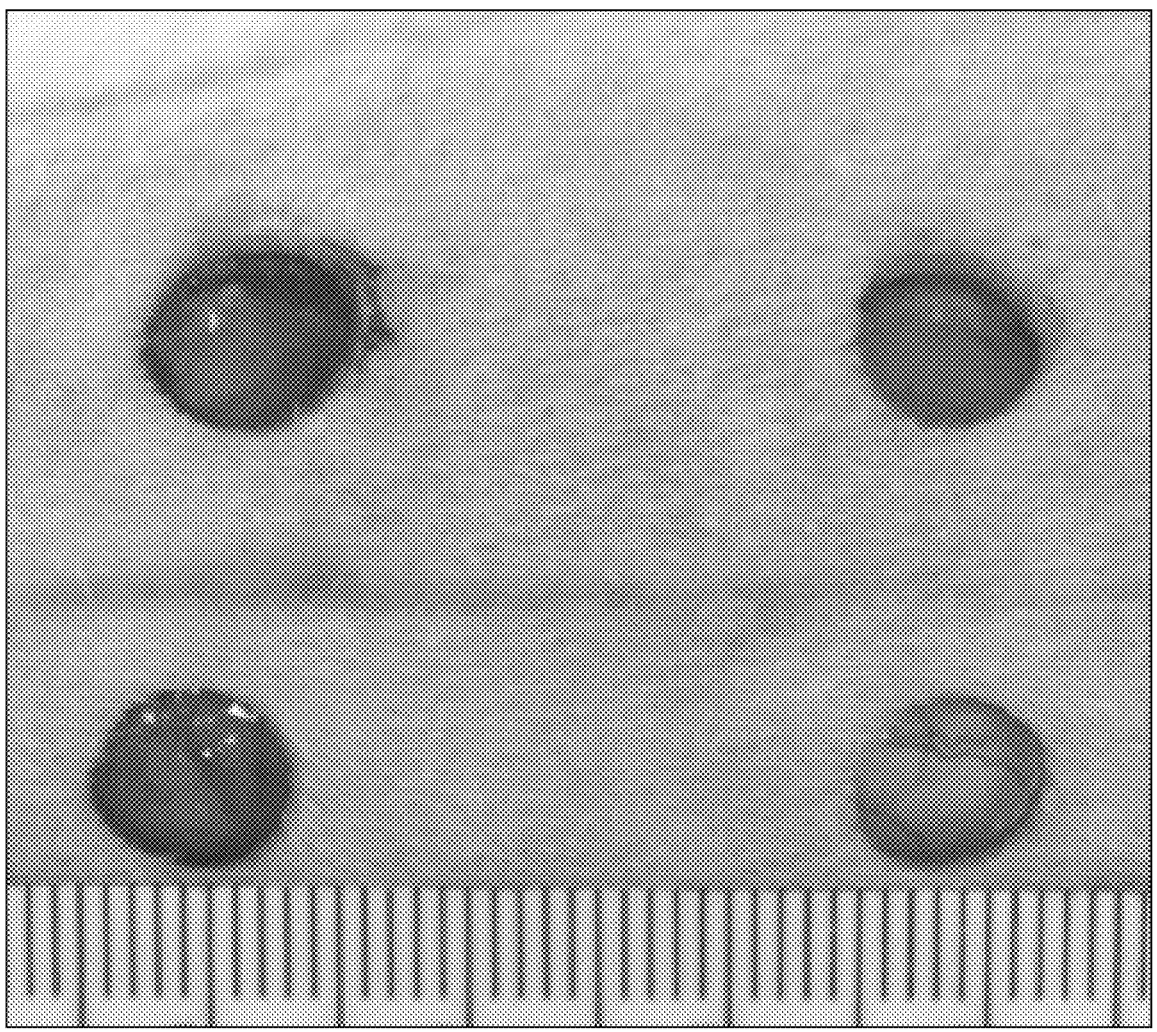
FIG. 5 shows damaged sites in a muscle damage animal model prepared in order to confirm a therapeutic effect against muscle damage.

As shown in FIG. 5, the four induced defect sites were divided into a total of four treated groups as shown in Table 1 below.

TABLE 1

| Group | Treatment |
| --- | --- |
| Group 1 (C) | Untreated control group |
| Group 2 (G) | Group treated with nitrogen gas alone |
| Group 3 (P30) | Group treated with nitrogen-based plasma for 30 sec |
| Group 4 (P60) | Group treated with nitrogen-based plasma for 60 sec |

Group 2 was treated with nitrogen gas alone, discharged through a nozzle, for 30 seconds without plasma discharge. The plasma irradiation device shown in FIG. 2 was fixed to the defect sites of groups 3 and 4, and then the defect sites were treated daily with the nitrogen-based plasma, produced in Experimental Example 1, for 30 seconds/day and 60 seconds/day over 7 days and 14 days, respectively, at a gas pressure of 10. After completion of the plasma treatment, the defect site tissues and the surrounding tissues were collected on day 7 or day 14. Using the collected tissues, whether the muscle defects would be restored was examined. Hereinafter, the group treated for 30 seconds will be referred to as P30, and the group treated for 60 seconds will be referred to as P60.

Example 1: Analysis of Cytotoxicity

For therapeutic use, whether irradiation with the nitrogen-based plasma would cause cytotoxicity was analyzed. Whether it would be cytotoxic was analyzed by visual tissue analysis, cell viability analysis and cytotoxicity analysis. For visual tissue analysis, observation of the tissue state of all the treated groups was continuously performed up to the end of the experiment in order to examine whether or not inflammation or foreign-body tissue would occur. The results of this visual observation are shown in FIG. 6.

Figure 6:
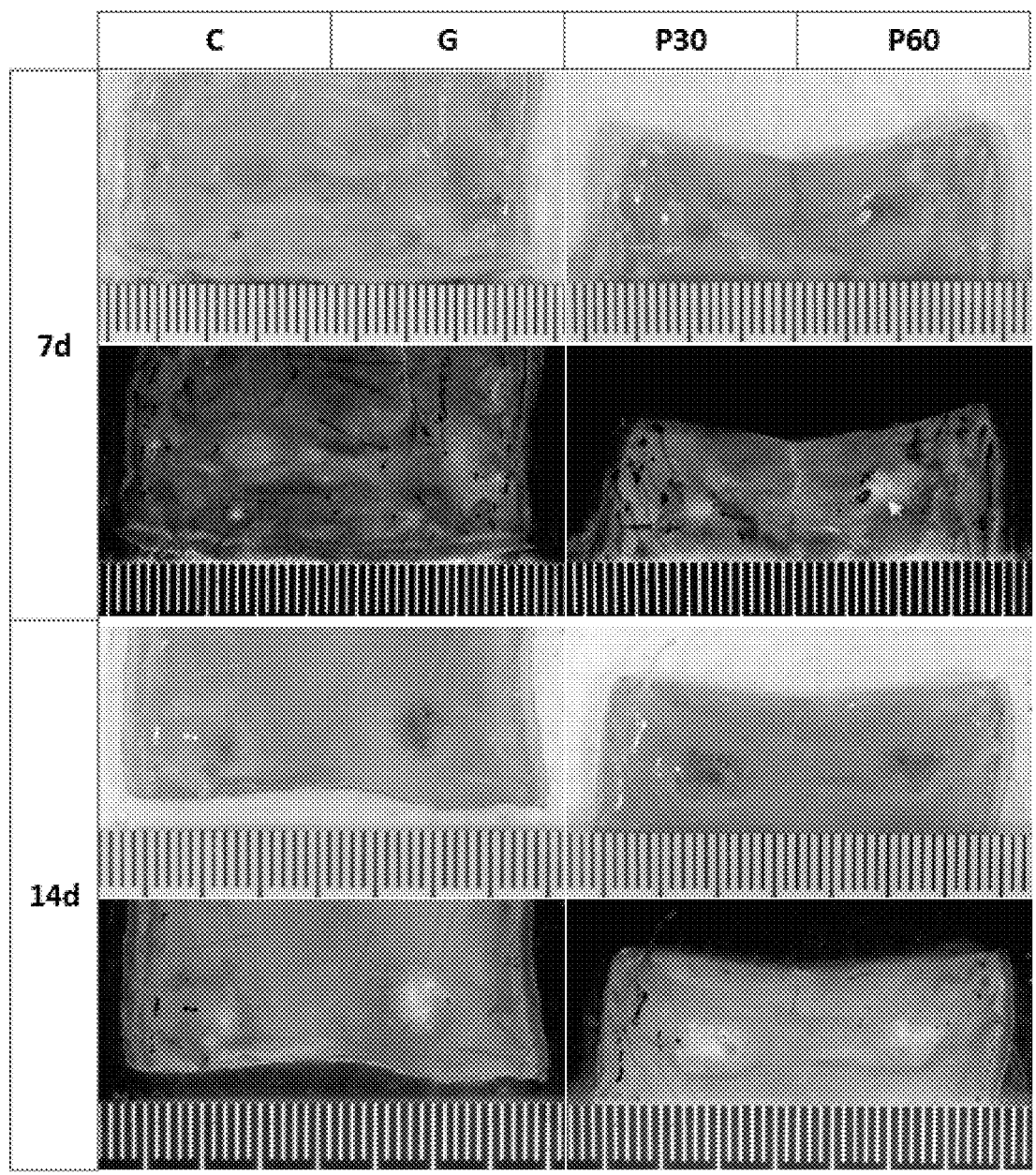
FIG. 6 shows the results of visually observing whether or not nitrogen-based non-thermal atmospheric pressure plasma treatment is cytotoxic. (C: untreated control group; G: group treated with nitrogen gas alone; P30: group treated for 30 seconds; P60: group treated for 60 seconds).

As shown in FIG. 6, clear inflammation or foreign-body tissue was not visually observed in all the four experimental groups.

Furthermore, muscle cells were cultured in differentiation medium and growth medium in vitro, and then treated with the nitrogen-based plasma of Experimental Example 1, and the state of cells in the treated groups and the untreated control group was analyzed by live/dead staining. The term "differentiation medium" refers to a medium having a composition for inducing differentiation of muscle cells that proliferated in vitro. In the present invention, the differentiation medium was configured such that it can induce cell differentiation by controlling the content of serum. The growth medium used in the present invention was a general cell growth medium having a composition making it possible to grow muscle cells in vitro. More specifically, the growth medium used was DMEM medium containing 10/o serum. The results of analysis of cell death are shown in FIG. 7.

Figure 7:
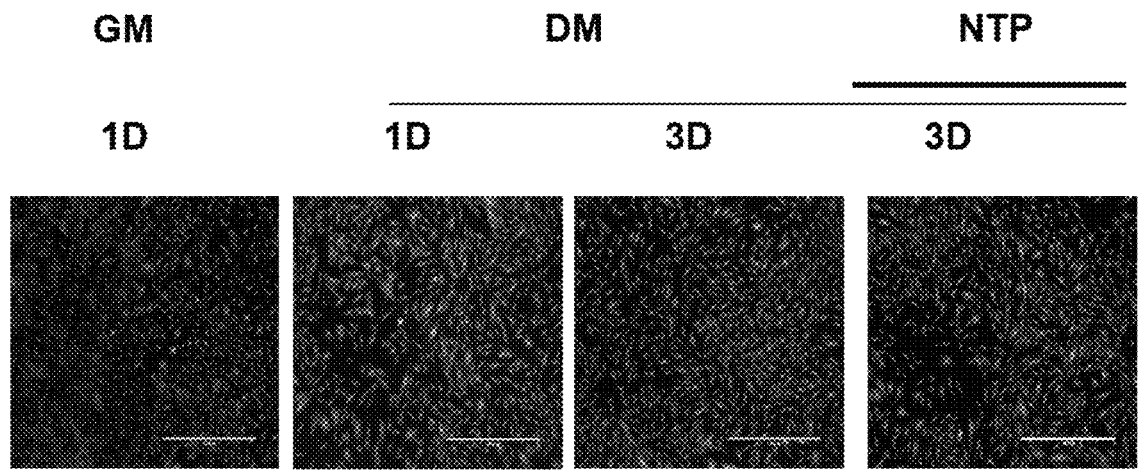
FIG. 7 shows the results of live/dead staining performed to examine whether or not nitrogen-based non-thermal atmospheric pressure plasma treatment of growth medium (GM) and differentiation medium (DM) is cytotoxic (C: untreated control group; G: group treated with nitrogen gas alone; P30: group treated for 30 seconds; P60: group treated for 60 seconds).

As shown in FIG. 7, dead cells (red color) were not observed in the muscle cells irradiated with the nitrogen-based plasma, and the irradiated cells were all live cells showing green fluorescence. Thus, it was found that the nitrogen-based plasma of the present invention is a safe material that causes no cytotoxicity.

Example 2: Examination of Muscle Damage Repair by Visual Observation and Tissue Staining To confirm muscle damage repair induced by treatment with the nitrogen-based plasma, visual observation and tissue staining were performed.

First, to visually observe tissue repaired/regenerated by irradiation with the nitrogen-based plasma, tissues were collected from all the treated groups on 7 and 14 days of nitrogen-based plasma irradiation and photographed, and then images thereof were analyzed. Images were captured using a digital camera and calculated using Metamorph_NX image software (Molecular Devices, Sunnyvale. California, USA). The average diameter of twenty muscle defect sites was 8.56±0.47 mm. The removed tissues were stained to verify the consistency of the muscle defects in the rats, and it was shown that the structures of the removed tissue contained muscle with the dermis lavers. To prevent treatment with the nitrogen-based plasma from affecting the untreated control group, the non-treatment sites were protected with surgical cloth during the plasma treatment. The distance between each defect site and the plasma nozzle was maintained at 0.4 cm, and the space between each defect site and the plasma irradiation device remained clogged by a shielding film.

As a result, it was observed that new capillary blood vessels were formed on the repaired tissue of the test group treated with P6 for 7 days. After 14 days, formation of new capillary blood vessels was visually observed on the images in all the test groups treated with the nitrogen-based plasma.

Figure 8:
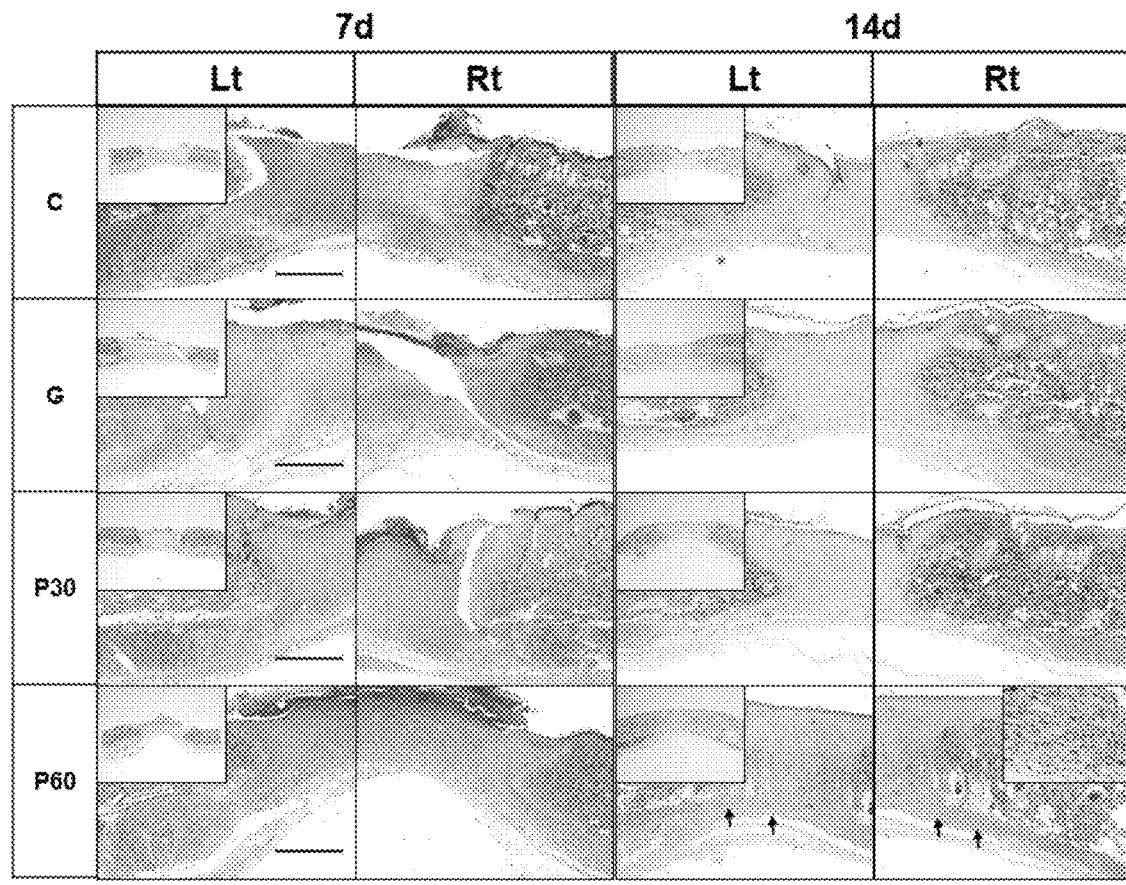
FIG. 8 shows the results of confirming new capillary blood vessel formation induced by nitrogen-based non-thermal atmospheric pressure plasma treatment (C: untreated control group; G: group treated with nitrogen gas alone; P30: group treated for 30 seconds; P60: group treated for 60 seconds).

For more specific observation, hematoxylin & eosin (H & E) staining, Picro Sirius red (PSR) staining, and Masson's trichrome (MT) staining were used H&E staining was used to stain the nucleus and cytoplasm of all the cells in tissue, thereby observing the stage of regeneration of the removed muscle tissue and the state of the cells. PSR staining was used for the purpose of morphologically distinguishing muscle tissue from the surrounding tissue. MT staining was performed to facilitate observation of newly formed muscle while showing the difference in color development between muscle tissue and the surrounding tissue. FIG. 8 shows the results of MT staining that stains muscle cells red.

As shown in FIG. 8, in both the P30 and P60 groups treated with the nitrogen-based plasma it was observed that the muscle defect sites were stained red after 7 days of the treatment, indicating that the muscle defect sites were repaired. The muscle tissue site stained red indicates that new muscle tissue was formed by treatment of the damaged muscle tissue with the nitrogen-based plasma. The test group treated with the nitrogen-based plasma for 14 days showed dearer and broader regenerated muscle sites compared to the group treated for 7 days.

Figure 9:
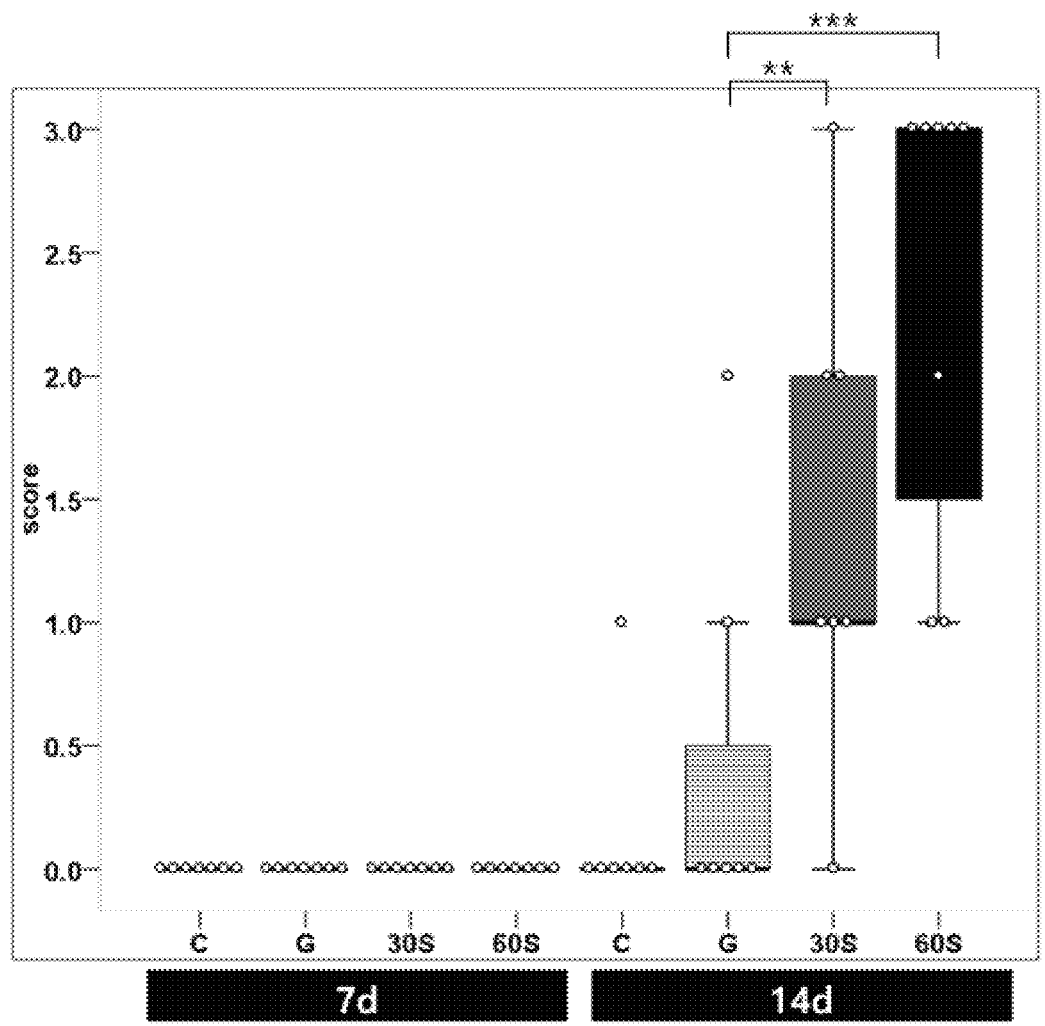
FIG. 9 shows the results of calculating the degree of muscle tissue regeneration using a standard score system (C: untreated control group: G: group treated with nitrogen gas alone: P30 group treated for 30 seconds; P60: group treated for 60 seconds)(P<0.01, *P<0.001).

To more objectively verify the degree of muscle tissue regeneration, the stained tissue was scored using a four-point standard score system as shown in Table 2 below, and the results are shown in FIG. 9.

TABLE 2

| score | Descriptions |
| --- | --- |
| 0 | Muscle expansion from wound margin is null. |
| 1 | Muscle expansion from wound margin is less than 25%. |
| 2 | Muscle expansion from wound margin is 25% to less than 50%. |
| 3 | Muscle expansion from wound margin is more than 50%. |

As shown in FIG. 9, after 14 days of the treatment, the P30 group showed muscle tissue regeneration corresponding to a score of 0.85±1.07, and the P60 group showed muscle tissue regeneration corresponding to a score of 1.86±1.21. These scores were statistically significant different from those of the untreated control group (0.14±0.38) and the group treated with nitrogen gas alone (0.43±0.78) ($P<0.01$, * $p<0.001$).

From these results, it can be seen that treatment with the nitrogen-based plasma promotes formation of new blood vessel and regeneration of muscle tissue in damaged muscle sites.

Example 3: Observation of Newly Formed Muscle by Immunohistochemical Analysis

It is known that when new muscle is formed, MyH-3 (nmyosin heavy chain-3) is expressed in the muscle cells and tissue. Thus, MyH-3 can be used as a marker for identifying new muscle. Accordingly, tissue was isolated from each of the animal groups, and the expression level of MyH-3 protein in the isolated tissue was measured by Western blot analysis. On 7 days and 14 days of the plasma treatment, expression of MyH-3 in the P60 group treated with the plasma for 60 seconds was analyzed, and the expression pattern of MyH-3 in the tissue was visualized by immunohistochemical staining.

Figure 10:
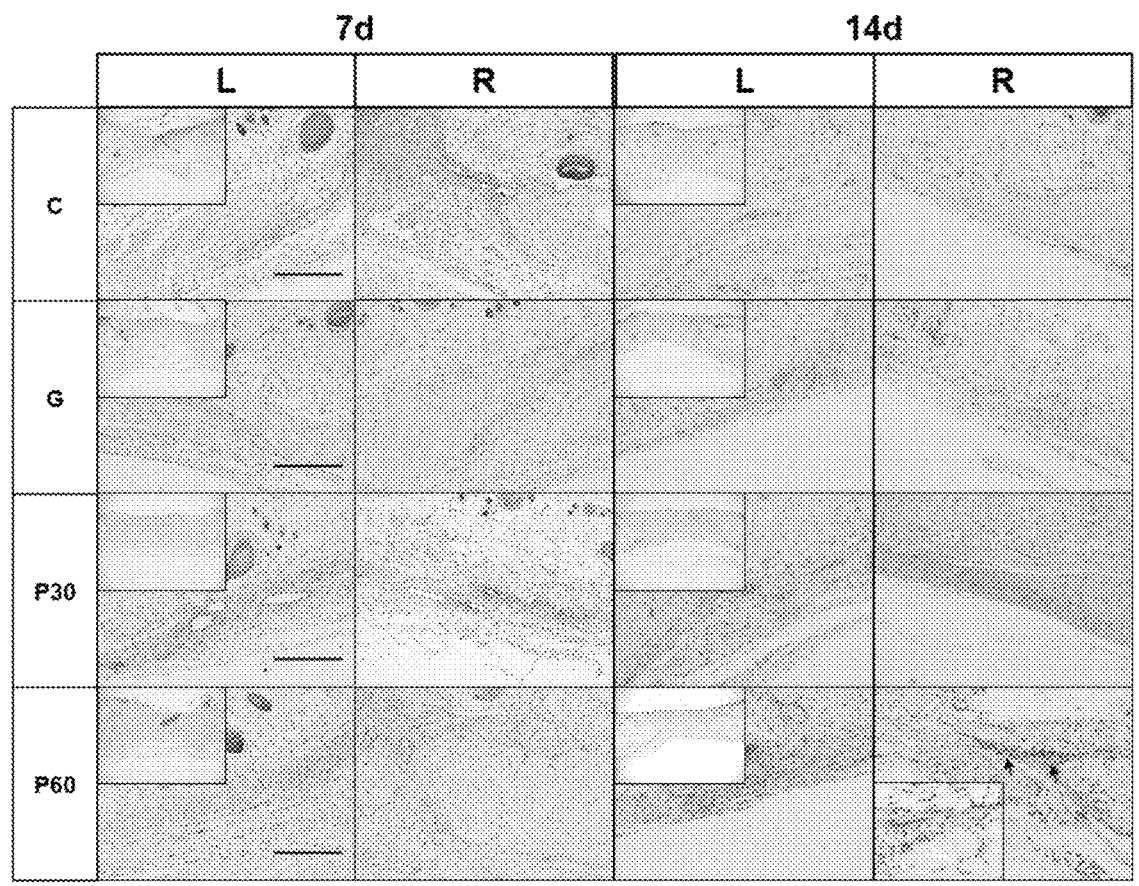
FIG. 10 shows the results of immunohistochemical staining performed to confirm muscle tissue regeneration (indicated by the arrow) induced by nitrogen-based non-thermal atmospheric pressure plasma treatment (C: untreated control group; G: group treated with nitrogen gas; P30: group treated for 30 seconds; P60: group treated for 60 seconds).

FIG. 10 shows the results of immunohistochemical staining. As shown in FIG. 10, it was found that in both the P30 and P60 groups, the MyHC-3 antibody was produced in the direction from the end of normal muscle to the damaged muscle site (i.e., the site from which muscle was removed), and thus the tissue was stained brown.

Figure 11:
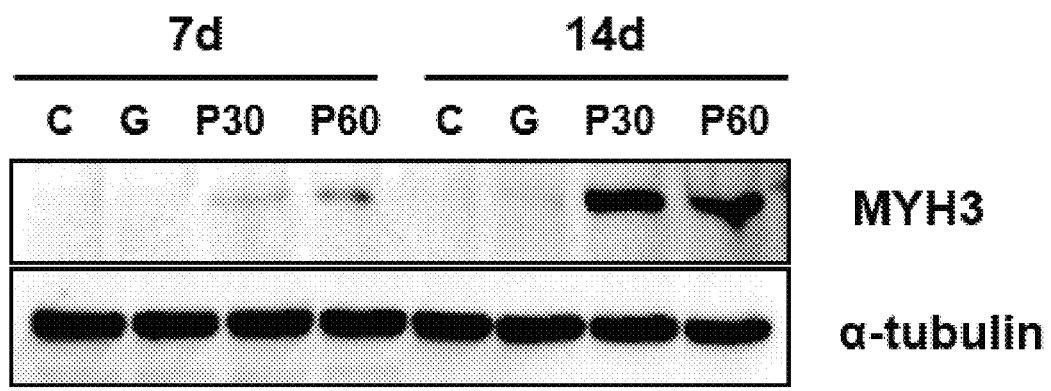
FIG. 11 shows the results of Western blot analysis for expression of MyHC-3 (C: untreated control group: G: group treated with nitrogen gas alone: P30: group treated for 30 seconds; P60: group treated for 60 seconds).

FIG. 11 shows the results of Western blot analysis for expression of MyHC-3. As shown in FIG. 11, it was fond that in the test groups treated with the nitrogen-based plasma for 30 second (P30) and 60 seconds (P60), respectively, over 7 days and 14 days, expression of MyHC-3 clearly increased.

From the results as described above, it can be seen that the tissue regenerated by treatment with the plasma-based plasma is muscle tissue. This suggests that even 1 to 2 weeks of treatment with the nitrogen-based plasma induces rapid formation of new muscle.

Example 4: Formation of Muscle Tissue and Induction of Cell Activation by Treatment with Nitrogen-Based Plasma To further investigate the effect of the nitrogen-based plasma on muscle cells and damaged muscle tissue, immunofluorescent staining images for each group were obtained and compared. To this end, activation of muscle cells in each tissue was examined by H&E staining. It is generally known that in the case of normal muscle, cells in muscle tissue are located at the periphery of muscle bundles, whereas in the case of newly formed muscle tissue, muscle cells are located in the center of muscle bundles by the muscle regeneration action of migrated cells. According, the position of muscle cells by treatment with the nitrogen-based plasma was analyzed. In addition, for the purpose of objectively observing the presence or absence of muscle in a tissue appearing to be muscle tissue, PSR (picro Sirius red) staining and MT staining % we performed Normal tissue is stained bright orange in PSR staining and stained red in MT staining, and other tissues are stained dark orange and blue. The results of staining by each of the staining techniques are shown in FIGS. 12 to 14.

Figure 12:
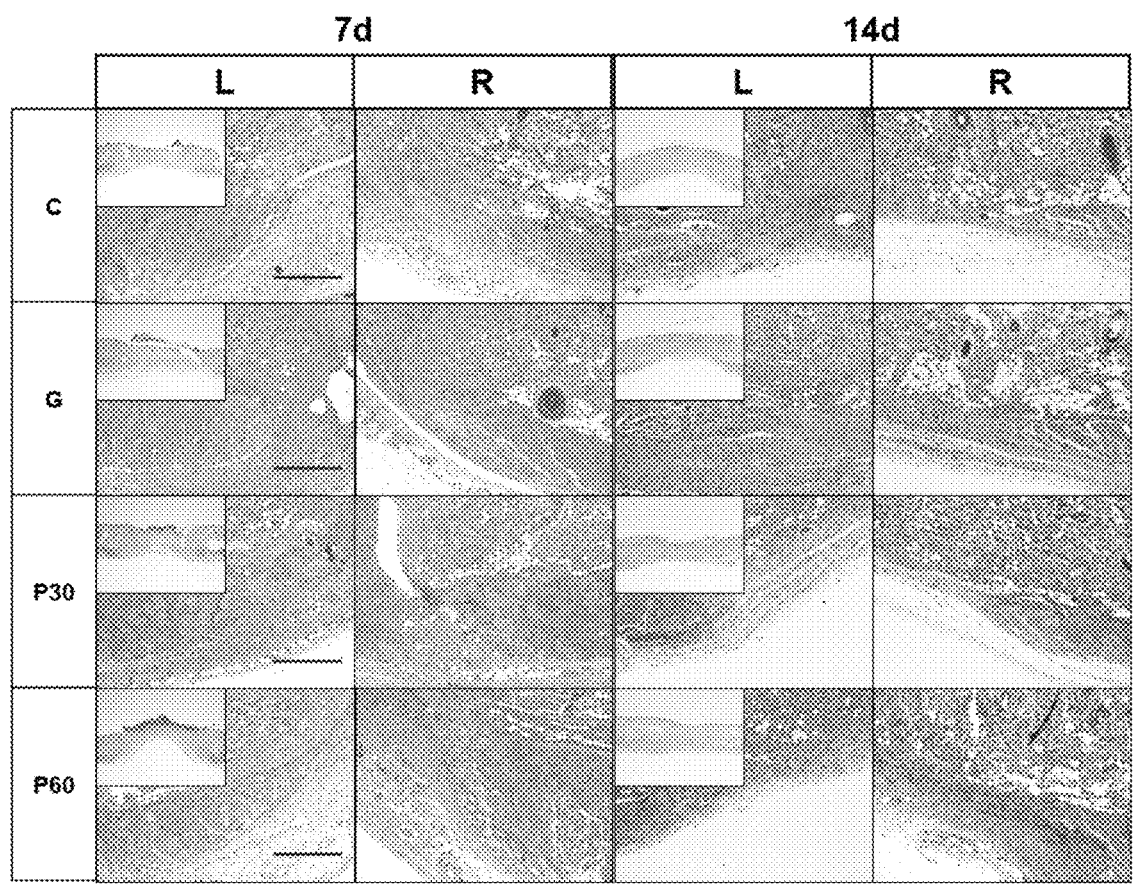
FIG. 12 shows the results of HE staining performed to confirm that a large amount of cells are clustered around muscle tissue after nitrogen-based non-thermal atmospheric pressure plasma treatment (C: untreated control group; G: group treated with nitrogen gas alone: P30: group treated for 30 seconds; P60: group treated for 60 seconds). Scale bar=1000 μm.
Figure 13:
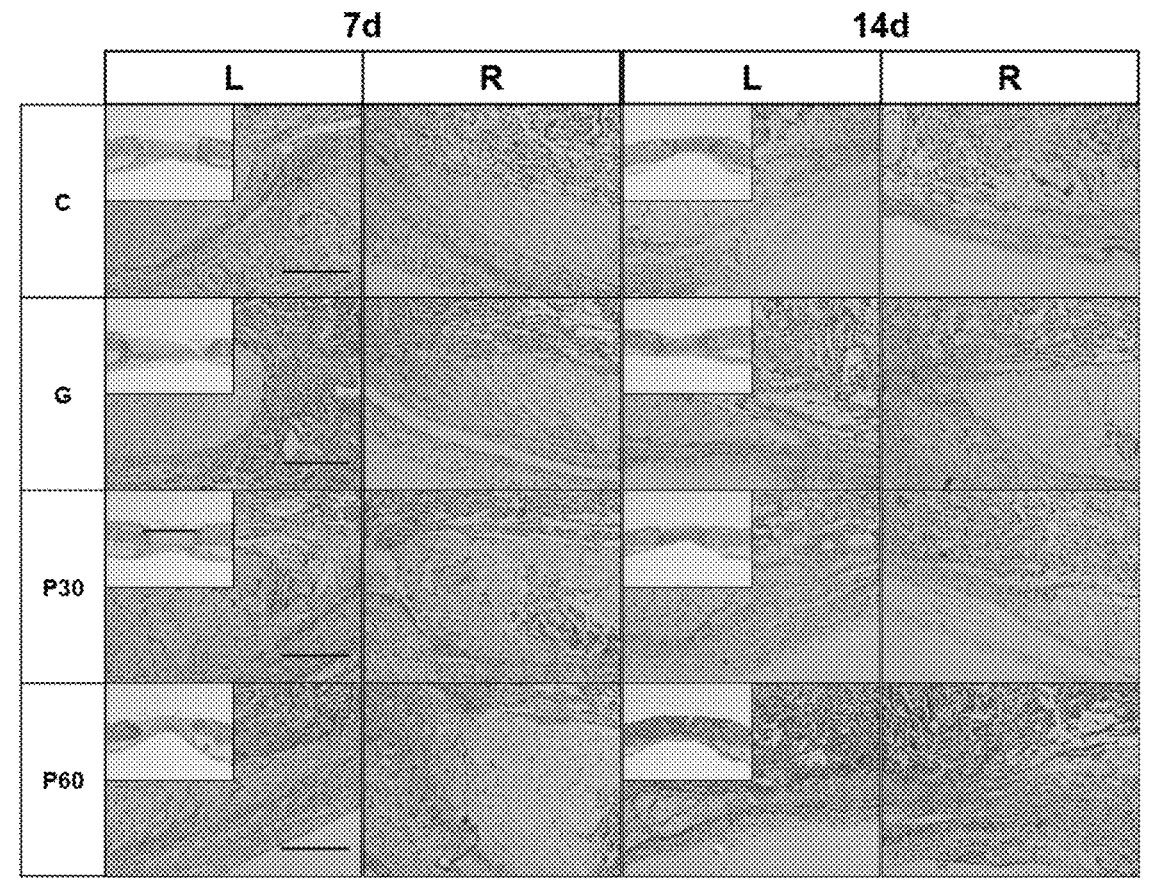
Figure 14:
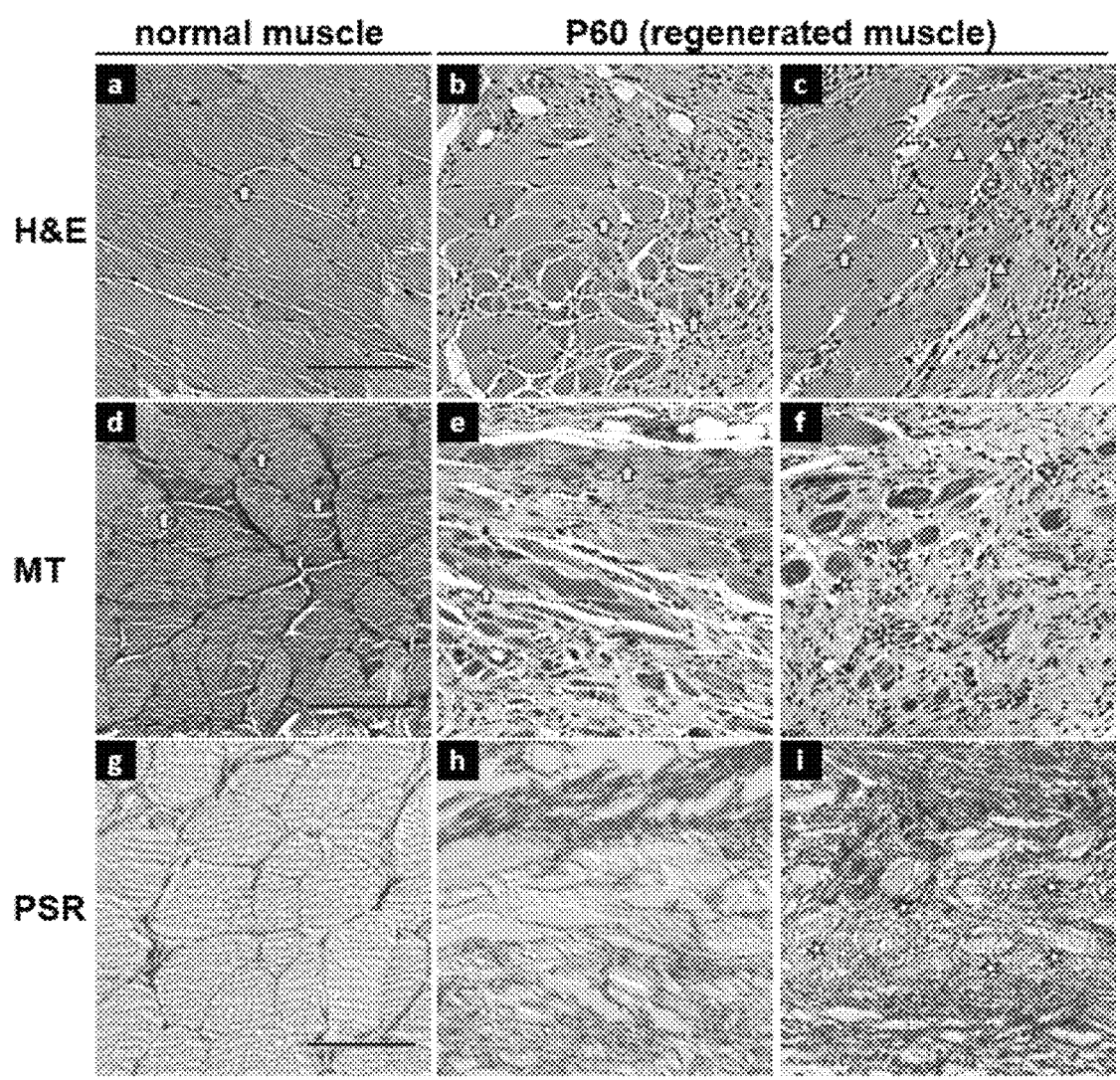
FIG. 14 shows the results of MT staining performed to confirm that muscle such as normal muscle tissue is formed after nitrogen-based non-thermal atmospheric pressure plasma treatment (arrow: cell cluster population located in muscle fibers; asterisk: small-caliber myofibers). Scale bar=100 μm.

As shown in FIGS. 12 to 14, in the P60 group treated with the nitrogen-based plasma for 60 seconds over 7 days and 14 days, it was observed that a large number of cells were clustered around damaged muscle tissue. In addition, it was observed that, at the distal end of normal tissue that borders with damaged muscle tissue, a tissue appearing to be a muscle tissue having a shape similar to that of normal muscle was formed, but cells in this tissue were located in the center, unlike normal muscle cells (FIG. 12). In addition, it was observed that a tissue appearing to be a new muscle formed by treatment with the nitrogen-based plasma was stained bright orange in PSR staining, clearly unlike other surrounding tissues, and was stained red in MT (Masson's trichrome) staining, indicating that it was stained very similar to normal muscle tissue (FIGS. 13 and 14). As can be seen in FIGS. 14e and 14h, in the P60 group on day 14, newly formed muscle fibers extending from the periphery of damaged muscle tissue were clearly observed. Furthermore, as can be seen in FIGS. 14f and 14i, small-caliber myofibers were observed (asterisk) in damaged muscle tissue. As can be seen in FIGS. 14b, 14c and 14e, myo-nuclei located in the center of newly formed myofibers were observed (arrow), and as can be seen in FIGS. 14a and 14d, these myo-nuclei were distinguished from myo-nuclei located in the periphery of normal myofibers.

These results suggest that the tissue restoration observed in damaged muscle tissue is attributable to muscle tissue regeneration induced by treatment with the nitrogen-based plasma, and it is achieved through muscle cell activation induced by treatment with the nitrogen-based plasma.

Example 5: Confirmation of Muscle Ce Activation Induced by Treatment with Nitrogen-Based Plasma It is generally known that muscle cells whose activation is in a resting state at the periphery of muscle bundles are converted into a proliferable and activated state when the muscle is damaged, after which these cells migrate to the periphery of the damaged muscle, and then proliferate and differentiate, thereby promoting muscle regeneration. Accordingly, observation was performed of the source of a large number of cells, which are clustered around damaged muscle by treatment with the nitrogen-based plasma, and the state of activation of the cells.

In order to identify the source and state of the clustered cells around damaged muscle as observed by H&E staining and PSR staining, immunohistochemical staining was performed using Pax 7 antibody, which is expressed in muscle satellite cells in a resting state and an activated state, and Ki-67 antibody which is expressed in growing cells.

Figure 15:
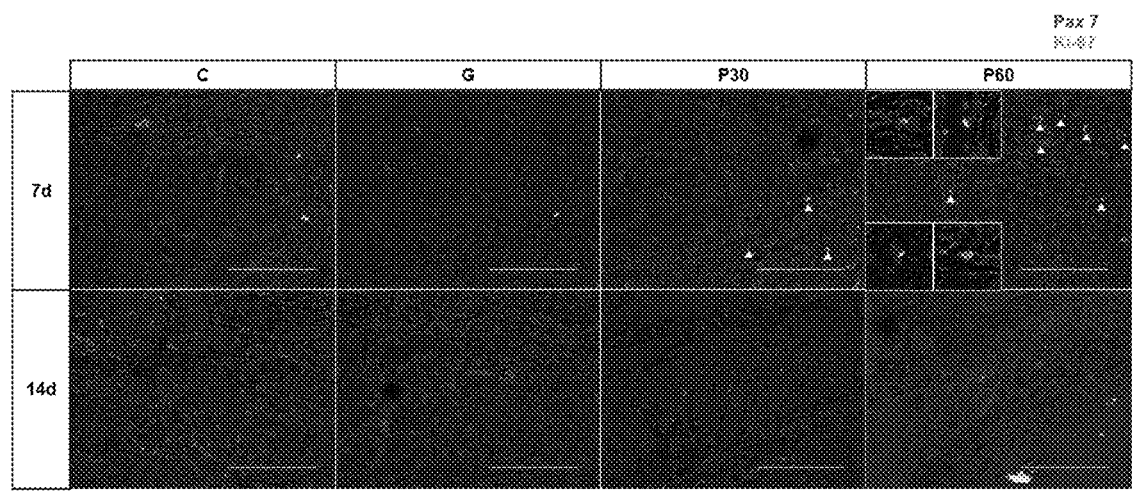
FIG. 15 shows the results of immunohistochemical staining performed using Pax 7 and Ki-67 antibodies in order to conform that muscle satellite cells are in an activated state after nitrogen-based non-thermal atmospheric pressure plasma treatment (C: untreated control group G: group treated with nitrogen gas; P30: group treated for 30 seconds; P60: group treated for 60 seconds).
Figure 16:
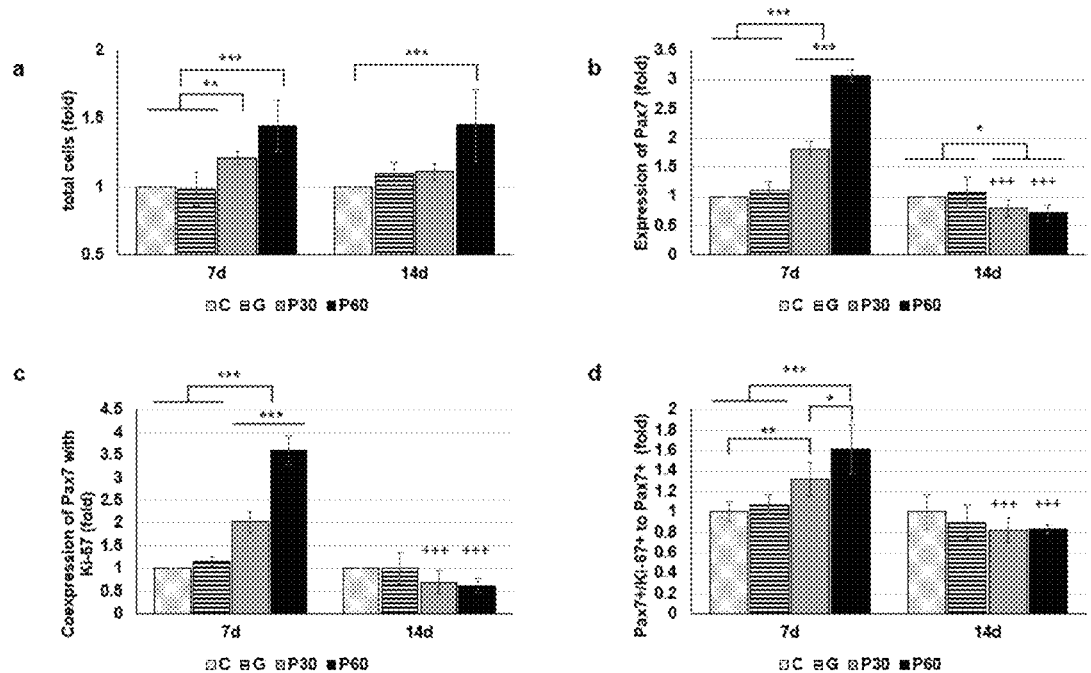
FIG. 16 shows increases (fold) in total cell number (a). Pax7 expression (b), coexpression of Pax7 and Ki-67 (c), and coexpression of Pax7+/Ki-67+ to Pax7 (d), which result from nitrogen-based plasma treatment. (*P<0.05, P<0.01, and *, +++P<0.001).

In the P30 group treated with the nitrogen-based plasma for 30 seconds over 7 days and the P60 group treated with the nitrogen-based plasma for 60 seconds over 7 days, the expression levels of the Pax7 and Ki-67 antibodies in the end of damaged muscles and the site with regenerated muscles were analyzed and quantified, and the results are show in FIGS. 15 and 16.

As shown in FIG. 15, Pax7 and Ki-67 were co-expressed, indicating that the clustered cells in damaged muscle and newly formed muscle are currently in an activated state that can proliferate into muscle satellite cells.

As shown in FIG. 16, the total numbers of cells in the groups treated with the nitrogen-based plasma were 1.2-fold (P30) and 1.4-fold (P60) of the control group on day 7. FIG. 16a shows the total number of cells; FIG. 16b shows the number of cells expressing Pax-7; FIG. 16c shows the number of cells co-expressing Pax-7 and Ki-67; and FIG. 16d shows the ratio of Pax-7 to the co-expressed antibodies. The numbers of Pax-7 positive cells in the P30 and P60 groups on day 7 were 1.8- and 3.1-fold larger than that in the control group. With the passage of time, the cell counts in the groups treated with the nitrogen-based plasma were significantly lower. The nuclei that stained positively with Ki67 were detected as proliferating satellite cells in the adjacent regenerating myofibers in the P30 and P60 groups on day 7 but were scarcely visible on day 14. Quantitative analysis of the immunostaining showed that coexpression of Ki-67 with Pax 7 in satellite cells in the P30 and P60 groups treated with the nitrogen-based plasma was 2.0 and 3.6 times higher than that in the control group on day 7, respectively. Similarly, as shown in FIG. 16d, Pax7+/Ki-67+ to Pax7 nuclei in the P30 and P60 groups were 1.3 and 1.6 greater in number than in the control group on day 7, respectively ($P<0.01$ and $P<0.001$). With the passage of time, the nuclei count in both P 30 and P 60 groups were significantly lower on day 14. In each quantitative analysis, no statistical differences were observed between the control group (C) and the group (G) treated with nitrogen gas alone, but the values in the P30 and P60 groups were significantly reduced on day 14 in every quantitative analysis except for that of total cells. These results show that treatment with the nitrogen-based plasma could increase the number of total cells, Pax7 expression and Pax7+/Ki-67+(proliferating satellite cells) coexpression. In connection with Pax3 which also a well-known satellite cell marker, the number of Pax3+/Ki67+ double positive cells also increased in the P30 and P60 groups.

Figure 17:
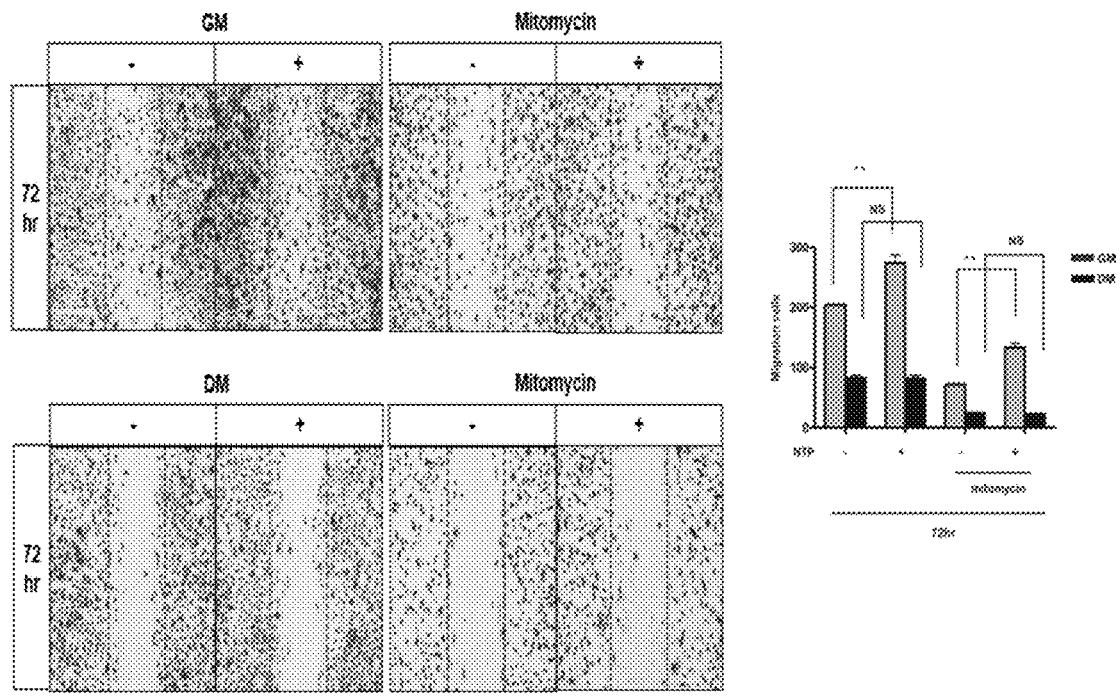
FIG. 17 shows the results of evaluating the effect of nitrogen-based non-thermal atmospheric pressure plasma treatment on cell migration in growth medium (GM) and differentiation medium (DM). ***P<0.001. Scale bar=1000 μm.
Figure 18:
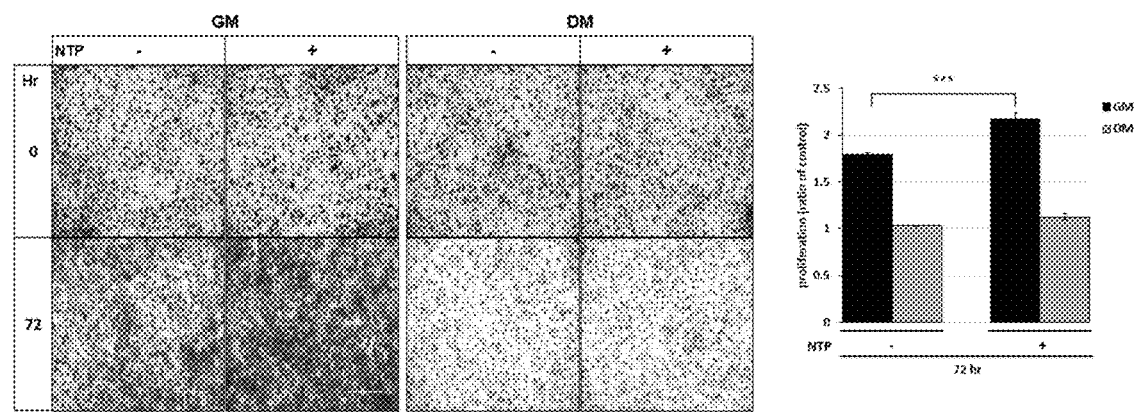
FIG. 18 shows the results of crystal violet staining and quantification performed to evaluate the effect of nitrogen-based plasma treatment on cell density. ***P<0.001. Scale bar=1000 μm.

Example 6: Examination of the Migration and Proliferation Patterns of Muscle Cells by Treatment with Nitrogen-Based Plasma In order to closely observe whether muscle cells actually migrate and proliferate by treatment with the nitrogen-based plasma, muscle cells were seeded in culture plates at a density of approximately $1.25 \times 10^5$ cells/cm and grown to confluence. Cell migration assays and cell proliferation assays were performed as described in Chang. J. W. et al. For quantitative analysis, cells on a plate (n=6) were captured with a digital imaging camera at each time point. The wound on the captured image was automatically recognized and measured by Metamorph® NX image software. Eluate of crystal violet staining was measured on a spectrum of 540 nm, and the results are shown in FIGS. 17 and 18. For in vitro proliferation and differentiation of human muscle cells, growth medium (GM) was used.

As shown in FIG. 17, the percentage of wound recovery area in the group treated with the nitrogen-based plasma was 61.31±6.3, which was 1.5 times higher than the percentage in the control group (42.27±4.13) in cell migration assays under the growth media (GM) condition at 72 hours in vitro. It was observed that the empty space in the cells treated with the nitrogen-based plasma was filled more than the untreated group on the growth medium, indicating that the recovery of the wound was more advanced.

As shown in FIG. 18, the number of cells after crystal violet staining was compared with the initial seeded cell number in order to determine the cell proliferation effect of the nitrogen-based plasma. As a result, it was shown that the fold increase in the cell number of the group treated with the nitrogen-based plasma was 2.17±0.01, which was significantly higher than that of the control group (1.79±0.02).

Figure 19:
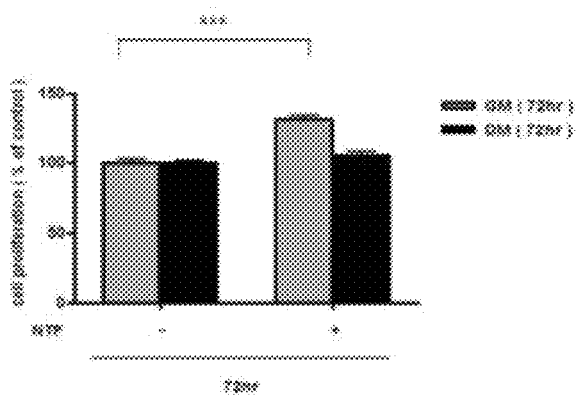
FIG. 19 shows the effect of nitrogen-based plasma treatment on in vitro cell to differentiation. ***P<0.001.

In addition, BrdU cell proliferation assay was performed to confirm that treatment with the nitrogen-based plasma could induce muscle cell proliferation, and the results are shown in FIG. 19.

As shown in FIG. 19, it was shown that treatment with the nitrogen-based plasma could induce muscle cell proliferation. These in vivo and in vitro results indicate that treatment with the nitrogen-based plasma can promote muscle cell proliferation and migration.

Example 7: Promotion of Muscle Cell Differentiation by Treatment with Nitrogen-Based Plasma It was found that the nitrogen-based plasma allows muscle cells to migrate to the borders of damaged muscle tissue. Accordingly, whether treatment with the nitrogen-based plasma can also induce muscle cell differentiation subsequent to promoting muscle cell migration and proliferation was analyzed in growth medium and differentiation medium using Pax 7 antibody, which is expressed in muscle satellite cells, MyoD which is expressed in the middle stage of muscle cell differentiation, and Myogenin (Myo G) antibody which is expressed in the late stage of differentiation. More specifically, primary normal human skeletal muscle myoblasts were obtained from Lonza and cultured to proliferate and differentiate. Undifferentiated cells in Clonetics Basal Medium and Bullet Kit medium were induced to differentiate by switching the medium to Dulbecco's modified essential medium supplemented with 2% horse serum, 2 mmol/L glutamines, and 50 U/mL streptomycin and penicillin. The cells' differentiation capacities were evaluated by expression of myogenic differentiation markers. To examine the relevance of treatment with the nitrogen-based plasma and muscle cell differentiation, observation was performed of coexpression of Pax7/MyoD and MyoD/MyoG, which are regarded as major markers of in muscle cell differentiation. The results of Western blot analysis and immunohistochemical staining are shown in FIGS. 20 and 21.

Figure 20:
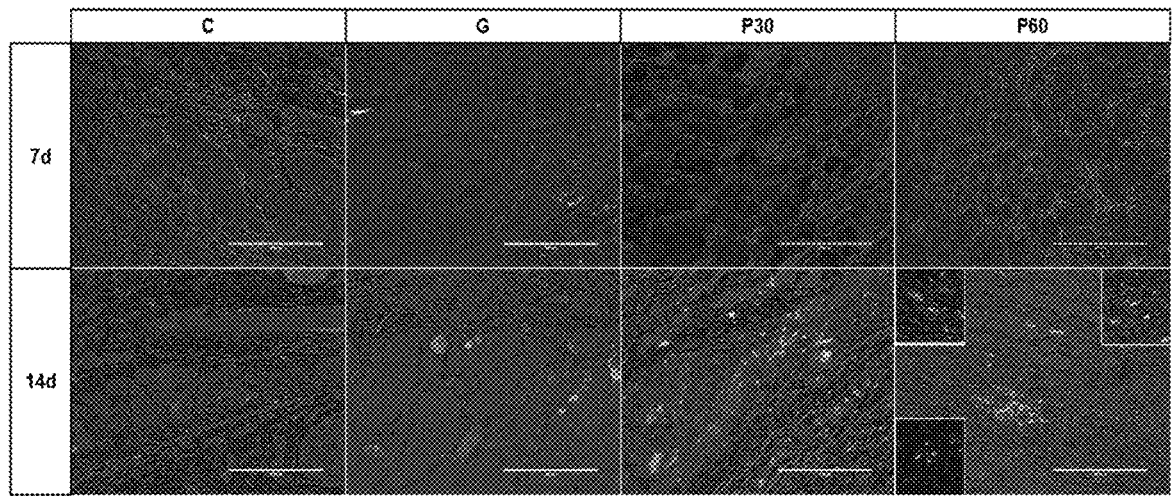
FIG. 20 shows the results of analyzing the expression of Pax 7 and Myo D antibodies, which results from nitrogen-based non-thermal atmospheric pressure plasma treatment (C: untreated control group: G: group treated with nitrogen gas alone; P30: group treated for 30 seconds; P60: group treated for 60 seconds). Scale bar=200 μm.
Figure 21:
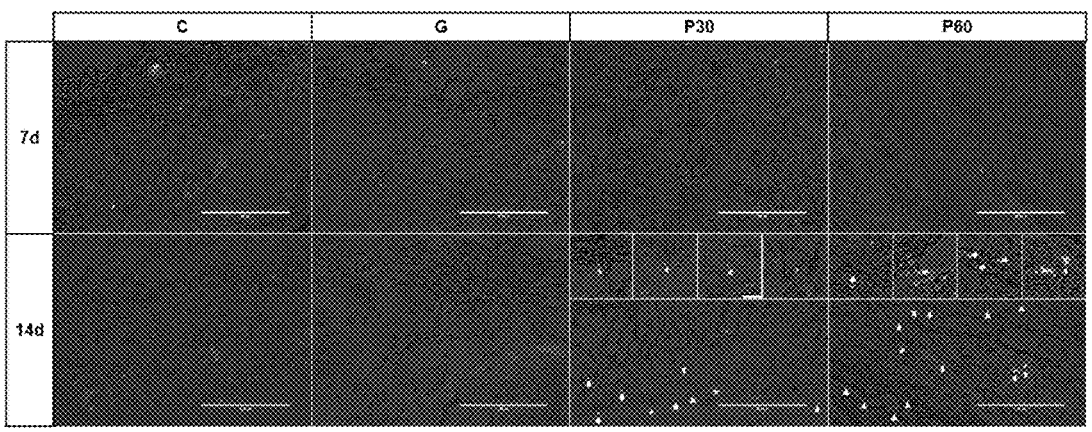
FIG. 21 shows the results of analyzing the expression of Myo D and Myo G antibodies, which results from nitrogen-based non-thermal atmospheric pressure plasma treatment (C: untreated control group: G: group treated with nitrogen gas alone; P30: group treated for 30 seconds, P60: group treated for 60 seconds). Scale bar=200 μm.

As shown in FIGS. 20 and 21, in the P60 group treated with the nitrogen-based plasma, coexpression of Pax7 and MyoD was detected on the borders of damaged tissue and newly formed muscle after 14 days (yellow). At the same time point, coexpression of MyoD and MyoG as a marker of late-stage muscle cell differentiation was also observed on the borders of damaged tissue and newly formed muscle in the P60 group (yellow). Such results revealed that treatment with the nitrogen-based plasma can promote not only muscle cell migration and proliferation in damaged muscle sites, but also muscle cell differentiation.

To examine the direct role of the nitrogen-based plasma in muscle cell differentiation, the cell phenotypes and the expression of proteins and mRNAs known to be involved in myogenesis were observed by Western blot analysis and MHC staining. The antibodies used in the Western blot analysis were as follows: MHC (myosin heavy chain) (R&D system, Minneapolis, USA), myogenin (Abcam. Cambridge. UK), creatin kinase M (Santa Cruz, California, USA), MET, p-p38, p38, p-AKT, AKT, and α-tubulin (Cell Signaling Technology, Danvers, Massachusetts, USA). PCR conditions were as follow denaturation for 3 min at 94° C., amplification for 35 cycles of 30 sec at 94° C., 60.7° C., and 72° C., and final extension for 5 min at 72° C. The human myogenin primer sequences used were as follows: F, 5-AGC GCC CCC TCG TGT ATG-3; R, 5-TGT CCC CGG CAA CT CAG C-3. The results are shown in FIGS. 22 and 23.

Figure 22:
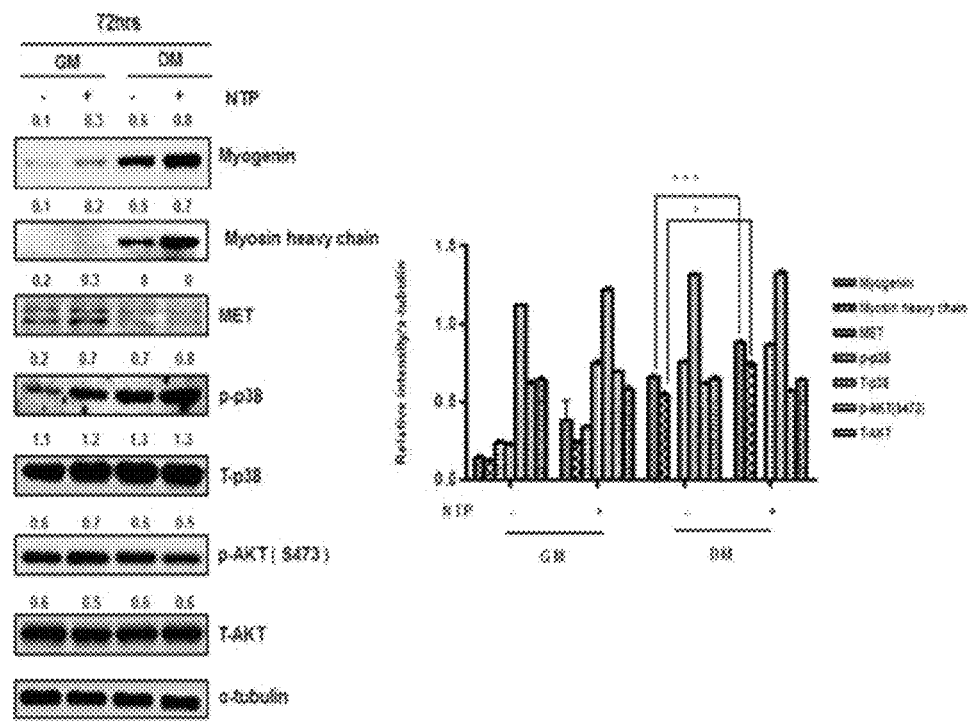
FIG. 22 shows the results of observing the change in expression of muscle satellite cell differentiation markers (myogenin and myosin heavy chain (MHC)) in growth medium (GM) and differentiation medium (DM), which results from nitrogen-based non-thermal atmospheric pressure plasma (NTP) treatment.

As shown in FIG. 22, when myoblasts were cultured in DM and treated with the nitrogen-based plasma, the cells became elongated and fused with nearby cells to form multinucleated tubes, and myogenin, myosin heavy chain (MHC), c-MET (HGFR), creatin kinase M, and p38 were high in the groups treated with the nitrogen-based plasma, and particularly, they were significantly higher when muscle cell differentiation was initiated. Based on these results, themolecular mechanisms by which NTP induced muscle differentiation was examined. Myosin heavy chain and myogenin expression was increased in the cells treated with the nitrogen-based plasma, whereas the expression of MET was unchanged in the differentiation medium condition. The intensity of the band was quantified and the values were presented as a graph. The results of Western blot analysis indicated that the expression of Myo D and Myogenin, which are muscle satellite cell differentiation markers, in the nitrogen-based plasma-treated cells in the differentiation medium, was higher than that in the untreated group.

Figure 23:
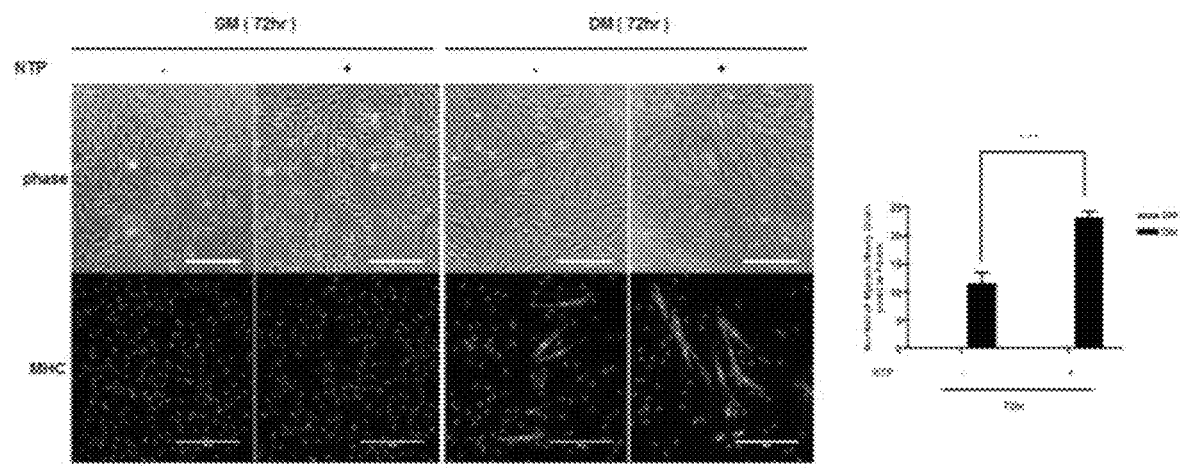
FIG. 23 shows the results of observing the increase in intracellular expression of myosin heavy chain (MHC) in differentiation medium (DM), which results from nitrogen-based non-thermal atmospheric pressure plasma (NTP) treatment.

The results of immune-fluorescence microscopy are shown in FIG. 23. As shown in FIG. 23, it was shown by MHC staining that the myotube formation with expression of MHC was increased by treatment with the nitrogen-based plasma. In addition, it was shown that the intracellular expression of myosin heavy chain was also higher in the group treated with the group treated with the nitrogen-based plasma, indicating that the cells were fused with each other. The results as described above indicate that treatment with the nitrogen-based plasma promotes muscle cell differentiation.

The results as described above show that the nitrogen-based plasma can promote muscle regeneration by non-invasive and non-contact biological stimulation, and induce muscle cell migration and proliferation in vivo and in vitro to form new muscle fibers, thereby effectively repairing muscle damage.

INDUSTRIAL APPLICABILITY

As described above, the nitrogen-based non-thermal atmospheric pressure plasma according to the present invention can effectively induce muscle cell activation, migration of muscle cells to damaged sites, muscle cell proliferation, and muscle cell differentiation, without surgical operation or during a treatment procedure after surgical operation, and thus can be advantageously used as a novel therapeutic agent and therapeutic method against muscle damage and muscle damage-associated diseases. Accordingly, the nitrogen-based non-thermal atmospheric pressure plasma is industrially applicable.

The invention claimed is:

1. A method for treating damaged muscles or promoting regeneration of damaged muscles, the method comprising a step of treating a damaged muscle site with a nitrogen-based non-thermal atmospheric pressure plasma for treating damaged muscles or promoting regeneration of damaged muscles, wherein the nitrogen-based non-thermal atmospheric pressure plasma is generated by a method comprising the steps of:

introducing nitrogen gas as a carrier gas;

applying a discharge initiation voltage of 5 to 10 kV to the introduced nitrogen gas at a frequency of 5 to 20 kHz, thereby producing the nitrogen-based non-thermal atmospheric pressure plasma; and maintaining a stable voltage of 1 to 10 kV after initiation of discharge.

2. The method of claim 1, wherein the nitrogen-based non-thermal atmospheric pressure plasma is discharged at 2 to 10 L/minute.

3. The method of claim 1, wherein the damaged muscle site is treated with the nitrogen-based non-thermal atmospheric pressure plasma at a distance of 0.3 to 5 cm.

4. The method of claim 1, wherein treatment with the nitrogen-based non-thermal atmospheric pressure plasma is performed for 10 to 120 seconds once a day.

5. The method of claim 1, wherein the treating of the damaged muscles or the regeneration of the damaged muscles is achieved by one or more selected from the group consisting of muscle cell activation, migration of muscle cells to a damaged site, muscle cell proliferation, and muscle cell differentiation.

6. The method of claim 1, wherein the treating of the damaged muscles is muscle repair.

* * * * *